United States Patent
Wang et al.

(10) Patent No.: US 7,941,204 B1
(45) Date of Patent: May 10, 2011

(54) MAGNETIC RESONANCE IMAGING CONCEPTS

(76) Inventors: Yi Wang, New York, NY (US); Pascal Spincemaille, New York, NY (US); Thanh D. Nguyen, New York, NY (US)

( * ) Notice: Subject to any disclaimer, the term of this patent is extended or adjusted under 35 U.S.C. 154(b) by 1363 days.

(21) Appl. No.: 11/281,920

(22) Filed: Nov. 16, 2005

Related U.S. Application Data

(60) Provisional application No. 60/628,614, filed on Nov. 16, 2004.

(51) Int. Cl.
  *A61B 5/05* (2006.01)
  *G01V 3/00* (2006.01)
(52) U.S. Cl. ......... 600/420; 600/410; 324/307; 324/309
(58) Field of Classification Search .................. 600/407, 600/410, 419–420; 324/306–309
  See application file for complete search history.

(56) References Cited

U.S. PATENT DOCUMENTS

| | | | | |
|---|---|---|---|---|
| 5,122,747 A * | 6/1992 | Riederer et al. | | 324/309 |
| 5,245,282 A * | 9/1993 | Mugler et al. | | 324/309 |
| 5,296,808 A * | 3/1994 | Macovski | | 324/309 |
| 5,485,086 A * | 1/1996 | Meyer et al. | | 324/307 |
| 5,534,777 A * | 7/1996 | Fuderer et al. | | 324/309 |
| 5,539,313 A * | 7/1996 | Meyer | | 324/309 |
| 5,561,370 A * | 10/1996 | Fuderer | | 324/309 |
| 5,652,516 A * | 7/1997 | Adalsteinsson et al. | | 324/309 |
| 5,810,726 A * | 9/1998 | Van Vaals et al. | | 600/410 |
| 6,201,985 B1 * | 3/2001 | Polzin et al. | | 600/411 |
| 6,307,368 B1 * | 10/2001 | Vasanawala et al. | | 324/309 |
| 6,381,486 B1 * | 4/2002 | Mistretta et al. | | 600/420 |
| 6,396,269 B1 * | 5/2002 | Hajnal et al. | | 324/307 |
| 6,404,194 B1 * | 6/2002 | Irarrazabal et al. | | 324/307 |
| 6,483,307 B2 * | 11/2002 | Ookawa | | 324/309 |
| 6,493,569 B2 * | 12/2002 | Foo et al. | | 600/410 |
| 6,671,536 B2 * | 12/2003 | Mistretta | | 600/410 |
| 6,750,651 B2 * | 6/2004 | Overall | | 324/309 |
| 6,828,788 B2 * | 12/2004 | Wang | | 324/309 |
| 6,914,429 B2 * | 7/2005 | Ookawa | | 324/309 |
| 7,003,343 B2 * | 2/2006 | Watts et al. | | 600/410 |
| 7,102,348 B2 * | 9/2006 | Zhang et al. | | 324/309 |
| 7,285,955 B2 * | 10/2007 | Roberts et al. | | 324/309 |
| 7,330,027 B2 * | 2/2008 | Kozerke et al. | | 324/307 |
| 2001/0004211 A1 * | 6/2001 | Ookawa | | 324/309 |
| 2003/0060698 A1 * | 3/2003 | Mistretta | | 600/410 |
| 2003/0135105 A1 * | 7/2003 | Jack et al. | | 600/410 |

(Continued)

OTHER PUBLICATIONS

J.Tsao et al.: "Eight-fold acceleration in real-time cardiac imaging using k-t BLAST and k-t SENSE with SSFP and segmented EPI". Proc.Intl.Soc.Mag.Reson.Med. 11, 2003, p. 209, XP002297010 conference' abstract.*

(Continued)

*Primary Examiner* — Long V Le
*Assistant Examiner* — Angela M Hoffa
(74) *Attorney, Agent, or Firm* — Scott E. Kamholz; Foley Hoag LLP

(57) ABSTRACT

Methods of acquiring magnetic resonance imaging (MRI) data for angiography. The present invention includes novel magnetization preparation schemes where the navigator and fat saturation pulses are executed in steady state after the preparatory pulses in order to minimize the delay between the magnetization preparation and the image echoes. The present invention also provides for improved methods of contrast-enhanced MRI where data are collected along non-linear trajectories through k-space and may also involve novel view ordering. In addition, the present methods employ novel motion corrections that minimize motion artifacts. The present invention further provides novel methods of self-calibrated sensitivity-encoded parallel imaging that allow for accurate and rapid scanning of subjects.

22 Claims, 23 Drawing Sheets

U.S. PATENT DOCUMENTS

| | | | |
|---|---|---|---|
| 2003/0153826 A1* | 8/2003 | Jack et al. | 600/410 |
| 2005/0007110 A1* | 1/2005 | Zhou | 324/307 |
| 2005/0070785 A1* | 3/2005 | Ahluwalia et al. | 600/410 |

OTHER PUBLICATIONS

J. Tsao et al.: "k-t BLAST and k-t SENSE: Dynamic MRI high frame rate exploiting spatiotemporal correlations" Mag.Reson.Med., vol. 50, No. 5, 2003; pp. 1031-1042.*

S.Kozerke et al.: "Accelerating Cardiac Cine 3D SSFP Imaging Using k-t BLAST with Integrated Training" Mag.Reson.Med., vol. 52, No. 1, 2004; pp. 19-26.*

Prince, M., et al., "Contrast-enhanced Abdominal MR Angiography: Optimization of Imaging Delay Time by Automating the Detection of Contrast Material Arrival in the Aorta", *Radiology*, vol. 203, No. 1, pp. 109-114, Apr. 1997.

Wilman, A., et al., "Fluoroscopically Triggered Contrast-enhanced Three-dimentional MR Angiography with Elliptical Centric View Order: Application to the Renal Arteries", *Radiology*, vol. 205, No. 1, pp. 137-146, Oct. 1997.

Wang, Y., et al., "Dynamic MR Digital Subtraction Angiography Using Contrast Enhancement, Fast Data Acquisition, and Complex Subtraction", *MRM*, vol. 36, pp. 551-556, 1996.

Henning, J., et al., "Time-Resolved Projection Angiographs after Bolus Injection of Contrast Agent", *MRM*, vol. 37, pp. 341-345, 1997.

Winchester, P., et al., "Comparison of Two-dimensional MR Digital Substraction Angiography of the Lower Extremity with X-Ray Angiography", *Society of Cardiovascular & Interventional Radiology*, vol. 9, No. 6, pp. 891-899, Nov./Dec. 1998.

Yoshikawa, T., et al., "Time-resolved two-dimensional thick-slice magnetic resonance digital subtraction angiography in assessing brain tumors", *Eur. Radiolo*, vol. 10, pp. 736-744, 2000.

Wang, Y., et al., "Contrast-Enhanced Peripheral MR Angiography from the Abdominal Aorta to the Pedal Arteries," *Investigative Radiology*, vol. 36, No. 3, pp. 170-177, 2001.

Korosec, F., et al., "Time-Resolved Contrast-Enhanced 3D MR Angiography", *MRM*, vol. 36, pp. 345-351, 1996.

Mistretta, C., et al., "3D Time-Resolved Contrast-Enhanced MR DSA: Advantages and Tradeoffs", *MRM*, vol. 40, pp. 571-581, 1998.

Riederer, S., et al., "MR fluoroscopy: technical feasibility", *Magn. Reson. Med.*, vol. 8, No. 1, pp. 1-15, Sep. 1988.

Peters, D., et al., "Undersampled Projection Reconstruction Applied to MR angiography", *Magnetic Resonsnace in Medicine*, vol. 43, pp. 91-101, 2000.

Vigen, K., et al., "Undersampled Projection-Reconstruction Imaging for Time-Resolved Contrast-Enhanced Imaging", *Magnetic Resonance in Medicine*, vol. 43, pp. 170-176, 2000.

Du, J., et al., "Time-Resolved, Undersampled Projection Reconstruction Imaging for High-Resolution CE-MRA of the Distal Runoff Vessels", *Magnetic Resonance in Medicine*, vol. 48, pp. 516-522, 2002.

Meyer, C., et al., "Fast Spinal Coronary Artery Imaging", *Magnetic Resonance in Medicine*, vol. 28, pp. 202-213, 1992.

Irarrazabal, P., et al., "Fast Three Dimensional Magnetic Resonance Imaging", *MRM*, vol. 33, pp. 656-662, 1995.

Nishimura, D., et al., "A Velocity k-Space Analysis of Flow Effects in Echo-Planar and Spiral Imaging", *MRM*, vol. 33, pp. 549-556, 1995.

Kerr, A., et al., "Real-Time Interactive MRI on a Conventional Scanner", *MRM*, vol. 38, pp. 355-367, 1997.

Amann, M., et al., "Three-Dimensional Spiral MR Imaging: Application to Renal Multiphase Contrast-Ehnahced Angiography", *Magnetic Resonance in Medicine*, vol. 48, pp. 290-296, 2002.

Spielman, D., et al., "Magnetic Resonance Fluoroscopy Using Spirals with Variable Sampling Densities", *MRM*, vol. 34, pp. 388-394, 1995.

Glover, G., "Simple Analytic Spiral K-Space Algorithm", *Magnetic Resonance in Medicine*, vol. 42, pp. 412-415, 1999.

Tasi, C., et al., "Reduced Aliasing Artifacts Using Variable-Density k-Space Sampling Trajectories", *Magnetic Resonance in Medicine*, vol. 43, pp. 452-458, 2000.

Kim, D., et al., "Simple Analytic Variable Density Spiral Design", *Magnetic Resonance in Medicine*, vol. 50, pp. 214-219, 2003.

Man L., et al., "Multifrequency Interpolation for Fast Off-resonance Correction", *MRM*, vol. 37, pp. 785-792, 1997.

Debbins, J., et al., "Cardiac Magnetic Resonance Fluoroscopy", *MRM*, vol. 36, pp. 588-595, 1996.

Pele, N., et al., "Outer Limits of Contrast-Enhanced MRA, Revised".

Deshpande, V., et al., "3D Magnetization-Prepared True-FISP: A New Technique for Imaging Coronary Arteries", *Magnetic Resonance in Medicine*, vol. 46, pp. 494-502, 2001.

Spuentrup, E., et al., "Navigator-Gated Free-Breathing Three-Dimensional Balanced Fast Field Echo (TrueFISP) Coronary Magnetic Resonance Angiography", *Investigative Radiology*, vol. 37, pp. 637-642, 2002.

Spuentrup, E., et al., "Navigator-Gated Coronary Magnetic Resonance Angiography Using Steady-State-Free-Precession Comparison to Standard T2-Prepared Gradient-Echo and Spiral Imaging", *Investigative Radiology*, vol. 38, pp. 263-268, 2003.

Foo, T., et al., "High Resolution Breath-hold Contrast-Enhanced 3D FIESTA Coronary Artery Imaging", *Proc. Intl. Soc. Mag. Reson. Med*, vol. 11, pp. 727, 2003.

Spuentrup, E., et al., "Impact of Navigator Timing on Free-Breathing Submillimeter 3D Coronary Magnetic Resonance Angiography", *Magnetic Resonance in Medicine*, vol. 47, pp. 196-201, 2002.

Huang, T., et al., "Are TrueFISP Images $T_2/T_1$-Weighted?", *Magnetic Resonance in Medicine*, vol. 48, pp. 684-688, 2002.

Hargreaves, B., et al., "Characterization and Reduction of the Transent Response in Steady-State MR Imaging", *Magnetic Resonance in Medicine*, vol. 46, pp. 149-158, 2001.

Scheffer, K., et al., "Magnetization Preparation During the Steady State: Fat-Saturated 3D TrueFISP", *Magnetic Resonance in Medicine*, vol. 45, pp. 1075-1080, 2001.

Wang, Y., et al., "Coronary MRI with a Respiratory Feedback Monitor: The 2D Imaging Case", *MRM*, vol. 33, pp. 116-121, 1995.

Wielopolski, P., et al., "Cardiac Imaging", *Radiology*, vol. 209, pp. 209-219, 1998.

Wang, Y., et al., "Algorithms for Extracting Motion Information from Navigator Echoes", *MRM*, vol. 36, pp. 117-123, 1996.

Jhooti, P., et al., "Phase Ordering With Automatic Window Selection (PAWS): A Novel Motion-Resistant Technique for 3D Coronary Imaging", *Magnetic Resonance in Medicine*, vol. 43, pp. 470-480, 2000.

van den Brink, J., et al., "Implications of SENSE MR in routine clinical practice", *European Journal of Radiology*, vol. 46, pp. 3-27, 2003.

Heidemann, R., et al., "A brief review of parallel magnetic resonance imaging", *EUR Radiol*, vol. 13, pp. 2323-2337, 2003.

Sodickson, D., et al., "Recent advances in image reconstruction, coil sensitivity calibration, and coil array design for SMASH and generalized parallel MRI", *Magnetic Resonance Materials in Physics, Biology and Medicine*, vol. 13, pp. 158-163, 2002.

Pruessmann, K., et al., "SENSE: Sensitivity Encoding for Fast MRI", *Magnetic Resonance in Medicine*, vol. 42, pp. 952-962, 1999.

Weiger, M., et al., "Sensitivity-Encoded Single-Shot Spiral Imaging for Reduced Susceptibility Artifacts in BOLD fMRI", *Magnetic Resonance in Medicine*, vol. 48, pp. 860-866, 2002.

Jaermann, T., et al., "SENSE-DTI at 3 T", *Magnetic Resonance in Medicine*, vol. 51, pp. 230-236, 2004.

Larkman, D., et al., "An Investigation into the Use of Sensitivity-Encoded Techniques to Increase Temporal Resolution in Dynamic Contrast-Enhanced Breast Imaging", *Journal of Magnetic Resonance Imaging*, vol. 14, pp. 329-335, 2001.

Bydder, M., et al., Combination of Signals From Array Coils Using Image-Based Estimation of Coil Sensitivity Profiles, *Magnetic Resonance in Medicine*, vol. 47, pp. 539-548, 2002.

Sodickson, D., "Tailored SMASH Image Reconstructions for Robust In Vivo Parallel MR Imaging", *Magnetic Resonance in Medicine*, vol. 44, pp. 243-251, 2000.

Jakob, P., et al., "Auto-SMASH: A self-calibrating technique for SMASH imaging", *Magnetic Resonance Materials in Physics, Biology and Medicine*, vol. 7, pp. 42-54, 1998.

Heidemann, R., et al., "VD-AUTO-SMASH Imaging", *Magnetic Resonance in Medicine*, vol. 45, pp. 1066-1074, 2001.

Griswold, M., et al., "Generalized Autocalibrating Partially Parallel Acquisitions (GRAPPA)", *Magnetic Resonance in Medicine*, vol. 47, pp. 1202-1210, 2002.

McKenzie, C., et al., "Self-Calibrating Parallel Imaging With Automatic Coil Sensitivity Extraction", *Magnetic Resonance in Medicine*, vol. 47, pp. 529-538, 2002.

Yeh, E., et al., "Self-Calibrated Spiral Parallel Imaging", *Proc. Intl. Soc. Mag. Reson. Med.*, vol. 10, 2002.

Pruessmann, K., et al., "Advances in Sensitivity Encoding With Arbitrary k-Space Trajectories", *Magnetic Resonance in Medicine*, vol. 46, pp. 638-651, 2001.

Lauzon, M., et al., "Polar Sampling in k-Space: Reconstruction Effects", *MRM*, vol. 40, pp. 769-782, 1998.

Glover, G., "Simple Analytic Spiral K-Space Algorithm", *Magnetic Resonance in Medicine*, vol. 42, pp. 412-415, 1999.

Wang, Y., "Description of Parallel Imaging in MRI Using Multiple Coils", *Magnetic Resonance in Medicine*, vol. 44, pp. 495-499, 2000.

Scheffler, K. et al., "Principles and applications of balanced SSFP techniques", *EUR Radiol*, vol. 13, pp. 2409-2418, 2003.

Duerk, J., et al., "Remember True FISP? A High SNR, Near 1-Second Imaging Method for T2-Like Contrast in Interventional MRI at .2T", *JMRI*, vol. 88, pp. 203-208, 1998.

Deshpande, V., et al., "3D Magnetization-Prepared True-FISP: A New Technique for Imaging Coronary Arteries", *Magnetic Resonance in Medicine*, vol. 46, pp. 494-502, 2001.

Sheffler, K., et al., "Magnetization Preparation During the Steady State: Fat-Saturated 3D TrueFISP", *Magnetic Resonance in Medicine*, vol. 45, pp. 1075-1080, 2001.

Scheffler, K., et al., "Contrast-Enhanced Angiography using T1-weighted TrueFISP", *Proc. Intl. Soc. Mag. Reson. Med.*, vol. 10, 2002.

Spuentrup, E., et al., "Navigator-Gated Free-Breathing Three-Dimensional Balanced Fast Field Echo (TrueFISP) Coronary Magnetic Resonance Angiography", *Investigative Radiology*, vol. 37, pp. 637-642, 2002.

Schreiber, W., et al., "Dynamic Contrast-Enhanced Myocardial Perfusion Imaging Using Saturation-Prepared TrueFISP", *Journal of Magnetic Resonance Imaging*, vol. 16, pp. 641-652, 2002.

Foo, T., et al., "MR Angiography Using Steady-State Free Precession", *Magnetic Resonance in Medicine*, vol. 48, pp. 699-706, 2002.

Hargreaves, B., et al., "Fat-Suppressed Steady-State Free Precession Imaging Using Phase Detection", *Magnetic Resonance in Medicine*, vol. 50, pp. 210-213, 2003.

Markl, M., et al., "Balanced Phase-Contrast Steady-State Free Precession (PC-SSFP): A Novel Technique for Velocity Encoding by Gradient Inversion", *Magnetic Resonance in Medicine*, vol. 49, pp. 945-952, 2003.

Herzka, D., et al., "Myocardial Tagging With SSFP", *Magnetic Resonance in Medicine*, vol. 49, pp. 329-340, 2003.

Wilman, A., et al., "Fluoroscopically Triggered Contrast-enhanced Three-dimensional MR Angiography with Elliptical Centric View Order: Application to the Renal Arteries", *Radiology*, vol. 205, pp. 137-146, 1997.

Scheffler, K., et al., "Eddy current optimized phase encoding schemes to reduce artifacts in balanced SSFP imaging", *Proc. Intl. Soc. Mag. Reson. Med.*, vol. 11, pp. 294, 2003.

Watts, R., et al., "Recessed Elliptical-Centric View-Ordering for Contrast-Enhanced 3D MR Angiography of the Carotid Arteries", *Magnetic Resonance in Medicine*, vol. 48, pp. 419-424, 2002.

Scheffler, K., "On the Transient Phase of Balanced SSFP Sequences", *Magnetic Resonance in Medicine*, vol. 49, pp. 781-783, 2003.

Hargreaves, B., et al., "Characterization and Reduction of the Transient Response in Steady-State MR Imaging", *Magnetic Resonance in Medicine*, vol. 46, pp. 149-158, 2001.

Nguyen et al., "Improved Magnetization Preparation for Navigator Steady-State Free Precession 3D Coronary MR Angiography," *Magnetic Resonance in Medicine*, 51:1297-1300 (Jun. 2004).

Qian et al., "Self-Calibrated Spiral SENSE," *Magnetic Resonance in Medicine*, 52:688-692 (Sep. 2004).

Spincemaille et al., "View Ordering for Magnetization Prepared Steady State Free Precession Acquisition: Application in Contrast-Enhanced MR Angiography," *Magnetic Resonance in Medicine*, 52:461-466 (Sep. 2004).

Zhu et al., "High Temporal and Spatial Resolution 4D MRA Using Spiral Data Sampling and Sliding Window Reconstruction," *Magnetic Resonance in Medicine*, 52:14-18 (Jul. 2004).

\* cited by examiner

MAGNETIC RESONANCE IMAGING CONCEPTS

"This invention was made with government support under Grant Nos. HL064647, HL062994, and HL060879 awarded by the National Institutes of Health. The government has certain rights in this invention." This statement is included solely to comply with 37 C.F.R. §401.14(f)(4) and should not be taken as an assertion or admission that the application discloses and/or claims only one invention.

BACKGROUND OF THE INVENTION

The present application claims the benefit under 35 U.S.C. 119(e) of U.S. Provisional Application No. 60/628,614 filed Nov. 16, 2004.

1. Field of the Invention

The field of the present invention generally relates to improvements in methods of magnetization preparation for collection of magnetic resonance imaging data and to improvements in methods of data collection of magnetic resonance imaging data from physiological tissue. In certain preferred embodiments, the present invention is directed to improved methods for performing magnetic resonance angiography.

2. Description of the Background

Magnetic resonance imaging (MRI) is a method of producing extremely detailed pictures of body tissues and organs that employs the inherent magnetic properties of the physiological tissue. MR angiography (MRA) is an MRI study of the vasculature for the purpose of detecting and diagnosing various disorders of the vasculature.

The scheme for magnetization of tissue for collection of MRA data is carefully chosen to improve the quality of the image obtained and to isolate data from particular types of tissues.

Real time or prospective navigator methods can be utilized to reduce motion artifacts in MRI without requiring the patient to hold a breath. Navigator echo is executed immediately before the image echo and is processed in real time to estimate motion information, which is then used immediately to guide image echo acquisition. The delay from the start of navigator echo to the beginning of image echo has to be sufficiently short to allow accurate estimation of motion in image echo and correspondingly effective suppression of motion artifacts in MR images. For example, this delay time should be less than 30 milliseconds for effective reduction of respiratory motion artifacts. An important field of application of the real time navigator method is cardiac imaging, including black blood imaging such as MRI of vessel wall and cardiac chamber, and white blood imaging such as cine MRI of the heart and coronary MRA.

Balanced steady-state free precession (SSFP) data acquisition provides short repetition time (TR) and high signal-to-noise ratio (SNR) for three dimensional (3D) coronary MRA and has been demonstrated to be advantageous over spoiled gradient echo approaches. Most previous SSFP 3D coronary MRA studies were performed within a breathhold. Recently, a navigator respiratory gating technique has been incorporated to overcome breathhold-related limitations. Because preparatory RF pulses (RFs) are required to drive spins into steady state prior to data acquisition, the reported navigator SSFP coronary sequences executed the navigator and fat saturation pulses before the preparatory RFs (Spuenturp, Bornert, Botnar, Groen, Manning, and Stuber, *Invest. Radiol.* 37:637-642, 2002).

In general, the separation between the navigator echo and the first image echo is approximately 100 ms. That delay may be too long to provide accurate motion information, leading to artifacts in the collected data. Furthermore, the separation between the fat saturation and the image echoes makes the fat suppression dependent on the field inhomogeneity, thereby degrading its effectiveness. Finally, the number of preparatory RFs is limited to approximately 20, which may not be a large enough number for adequate SSFP signal contrast and sufficient reduction of signal oscillation in the case of a set of linearly ramped preparatory RF pulses.

Additional applications of MRI techniques include the use of contrast agents to improve signal detection and, specifically, contrast-enhanced magnetic resonance angiography (CEMRA) has become the method of choice for performing MRA. A typical CEMRA examination completes in 20-30 seconds and requires timing data acquisition to contrast arrival using a test injection or real-time monitoring. These timing procedures complicate the task of performing CEMRA and, though quite reliable, are not without possible error. Time-resolved data acquisition methods which capture the passing of the contrast bolus through the arteries, organ, and veins of interest have the advantage of eliminating the need for bolus timing while simultaneously mapping blood flow dynamics. However, typical 3D k-space sampling of the required high spatial frequency for depicting vascular details takes too long (10-20 seconds) to provide acceptable temporal resolution.

By discarding the sampling of depth resolution, 2D projection MRA can be completed in one second, thereby providing adequate temporal resolution with high in-plane resolution in a manner similar to conventional projection X-ray digital subtraction angiography (DSA). Such 2D projection magnetic resonance digital subtraction angiography (MRDSA) has been utilized for visualizing arterial venous malformation, resolving arteries in distal extremities, and providing timing information for bolus chase data acquisition in peripheral MRA. However, the lack of depth resolution limits the clinical utility of the 2D projection MRDSA.

Since the signal on 3D MRA is largely located in the center of k-space and since sparse bright voxels in MR angiograms allow undersampling in k-space, time resolved imaging of contrast kinetics (TRICKS) methods have been developed to provide adequate temporal resolution for 3D MRA while preserving high spatial resolution. Particularly, the radial k-space sampling (PR TRICKS) allows natural azimuthal undersampling and sliding window reconstruction. The PR TRICKS approach provides adequate temporal resolution with high 3D spatial resolution, promising vast clinical potential.

It should be noted that the sliding window expands to about 20 seconds for sampling a full, high-resolution k-space data set. Furthermore, the radial sampling is limited to sampling one straight spoke per RF excitation, which results in suboptimal SNR efficiency. Spiral sampling can substantially shorten the scan time and also allows azimuthal undersampling and sliding window reconstruction. Thus, there has been a recognized need in the medical imaging community for a data collection scheme that allows for improved temporal and spatial resolution.

Generally, SSFP imaging provides high SNR and fast speed and is being adopted in many clinical applications with additional magnetization preparation to enhance desired image contrast. When magnetization preparation pulses are inserted into an SSFP sequence, data acquisition becomes segmented and view ordering is required to maximize the signal contrast during the acquisition of the center of k-space.

However, the repetition-to-repetition changes in phase encoding gradients cause spin phase variations associated with gradient-induced eddy currents and consequently lead to artifacts in SSFP imaging. The changes in phase encoding gradients from one repetition to the next have to be kept small to minimize these artifacts.

Bright background signal is also a major concern in SSFP CEMRA because of the T2/T1 tissue contrast. Such a bright background signal can be suppressed by adding a magnetization preparation into the SSFP sequence. A periodic insertion in the RF train of an inversion pulse, immediately followed by preparatory RFs with disabled data acquisition (disdacqs) will suppress tissues with long T1 relaxation. However, the temporal variations in blood and background signals after each inversion pulse may cause image artifacts and abate background suppression. These problems may be alleviated by matching the order of sampled k-space views to the variation in signal. The MRA field generally recognizes that an improved view order should satisfy two competing demands: 1) the central portion of k-space is acquired during the background signal nulling to optimize background suppression; and 2) the sampling trajectory in the phase and slice encoding space ($k_y k_z$-space) is smooth to minimize artifacts associated with gradient induced eddy currents.

Further clinical MRA applications employ multiple RF channel parallel imaging using coil sensitivity encoding (SENSE). The standard procedure for performing SENSE consists of: 1) acquisition of a fully sampled reference scan for coil sensitivity estimation; and 2) accelerated acquisition of an undersampled scan for the targeted application. The reference scan for coil sensitivity increases the total scan time and may cause misregistration artifacts if the patient moves between the reference scan and the accelerated data acquisition. It is highly desirable to eliminate the reference scan by estimating the coil sensitivities from the accelerated acquisition itself.

Such self-calibration techniques have been developed for a parallel imaging variant—SMASH. In the Cartesian sampling trajectory case, additional views in the central region of k-space are acquired to construct a low resolution image with minimal wrapping artifacts. In the spiral imaging trajectory case, the high sampling density near k-space center naturally allows the reconstruction of a low resolution image with little artifacts. No additional spiral interleaf is required. Thus, there has been a clear need in the prior art for an improved parallel imaging variant SENSE technique that provides for rapid image collection and appropriate calibration without additional scans.

Time-resolved high resolution 3D MRI generates a huge amount of data for reconstruction. Multiple RF coil reception further extends the amount of computation for reconstruction. In the case of data sampled on non-Cartesian trajectories, such as spiral, reconstruction computation is substantially increased by regridding and off-resonance correction.

SUMMARY OF THE INVENTION

In accordance with the present invention, there are provided methods for MRI data collection and reconstruction.

One aspect of the present invention is an effective navigator method for MRI with magnetization preparation and navigator by minimizing the delay between the navigator echo and the image echo, allowing accurate motion estimation and correspondingly effective gating and correction of motion artifacts in image echoes. One embodiment of navigator steady-state free precession (SSFP) is three-dimensional coronary MRA. In this preferred embodiment, the navigator and fat saturation pulses are preferably executed in steady state after the dummy or preparatory RF pulses so that the delay between the magnetization preparation and image echoes are minimized. Compared with previous preparation schemes, the present invention provides more effective motion suppression, significantly improved blood-to-myocardium contrast-to-noise ratio at slightly but insignificantly decreased blood SNR, significantly reduced fat SNR, and better overall image quality.

Alternatively, the preparatory RF pulse set can be shortened by optimizing the phases and amplitudes of these RF pulses. For example, six RF amplitudes ramped up according to the Kaiser-Bessel window function in approximately 24 milliseconds can effectively establish steady state for SSFP imaging, thereby allowing effective respiratory navigator gating and correction. In another embodiment of black blood imaging where double inversion precedes image echo acquisition by 300-600 milliseconds, the navigator echoes can be acquired before the double inversion, during the waiting, and immediately before and after the image echoes, to allow accurate tracking of motion and correspondingly effective motion compensation.

The present invention further provides for a method of time-resolved MRI data sampling that improves upon prior art methods by increasing temporal resolution and SNR through using non-linear k-space trajectories. This aspect of the present invention includes sliding window reconstruction with complex subtraction of precontrast mask data and improved off-resonance correction for time resolved 3D spiral MRA. The non-linear trajectories may be spiral, and the scan time and sliding window duration are reduced compared to the linear k-space sampling trajectory used in the prior art. That aspect of the present invention also includes cardiac-phased resolved study of the heart using bright or black blood pulse sequences.

The present invention still further provides for view ordering schemes that satisfy both image contrast maximization and image artifacts minimization in MRI. In one embodiment, the view order is used to maximize image contrast and minimize eddy current artifacts in magnetization prepared steady state free precession imaging that is used for time resolved contrast enhanced MRA to capture the contrast bolus in the arteries or cardiac phase resolved MRI to study the function of the heart. This view order is further compatible with real time navigator gating algorithms that smoothly distribute motion in k-space.

The present invention also provides for methods that allow for the self-calibration of coil sensitivity during data collection runs, thus greatly increasing the SNR and temporal resolution of MRI. The present invention further provides methods for rapid reconstruction of a large number of image volumes from all temporal phases of data collected with multiple RF coils using parallel computing over multiple processors.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein:

FIG. 12D shows data acquisition according to the present invention using lines of constant slice encoding $k_z$ with an empty circle denoting the first acquired view after an inversion and a solid circle denoting a central view and the full and dashed lines representing the view ordering trajectory of two successive segments;

DETAILED DESCRIPTION OF THE INVENTION

It is to be understood that the figures and descriptions of the present invention have been simplified to illustrate elements that are relevant for a clear understanding of the invention, while eliminating, for purposes of clarity, other elements that may be well known. The detailed description will be provided hereinbelow with reference to the attached drawings.

One aspect of the present invention relates to an improved navigator protocol for magnetization prepared steady-state free precession 3D coronary MRA. In a presently-preferred embodiment, the magnetization preparation method that executes the navigator echo and the fat saturation just prior to the image echoes. The present scheme allows more effective motion and fat suppression and improved contrast-to-noise ratio for coronary MRA.

Figure 1:
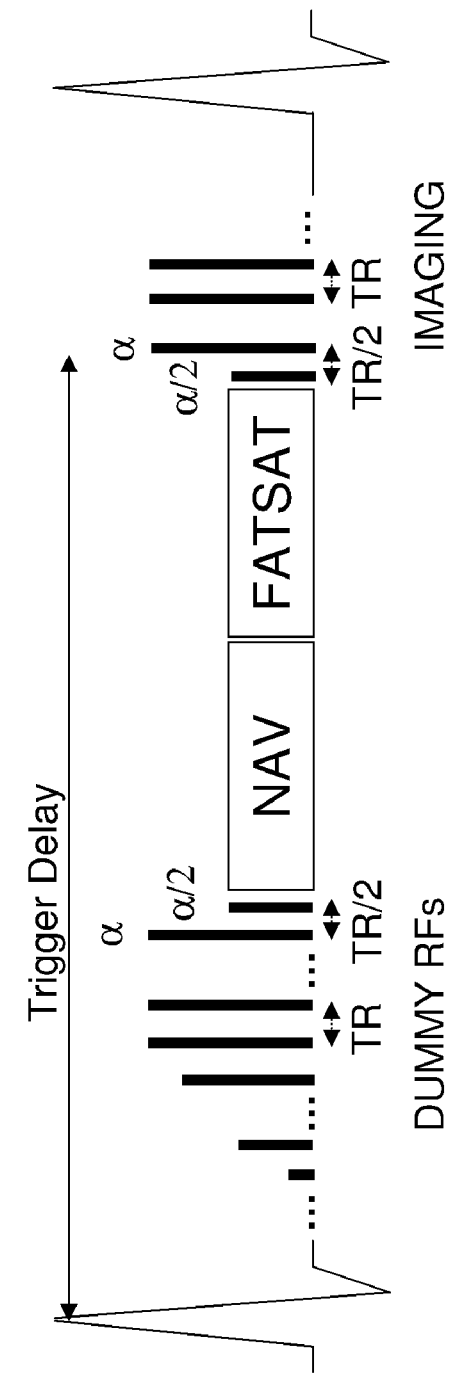
FIG. 1 shows a navigator (NAV) and magnetization preparation (FATSAT) protocol of the present invention.

In one implementation of navigator steady-state free precession 3D coronary MRA, the navigator and fat saturation pulses are executed during steady state after the preparatory RFs (FIG. 1). The α/2 pair is used to conserve the steady state. The fat saturation pulse is executed immediately before the start of data acquisition, which minimizes the fat signal regrowth during imaging. The separation between the navigator echo and the first image echo is approximately 20 ms (compared to approximately 100 ms in the prior art scheme), thus providing accurate information on motion occurring during data acquisition. The number of preparatory RFs is only limited by the trigger delay, allowing a large number of preparatory RFs. In one presently-preferred embodiment, 60 preparatory RF pulses (consisting of 30 linear ramp-ups and 30 constant flip angles) were used to establish steady state, compared to 20 linear ramp-ups in the prior art scheme.

A set of experiments comparing the performance of the new preparation scheme with that of the previous scheme were performed on seven healthy adults (mean age of 28±5 years) using a 1.5 Tesla whole-body MR system. The subjects were examined supine with peripheral pulse gating during free breathing. A four-element phased-array cardiac coil (two anterior, two posterior elements) was used for signal reception. For the purposes of navigator positioning and coronary artery localization, gradient echo scout scans were performed to localize the diaphragm and to identify the orientation of the atrioventricular sulcus and the interventricular groove. The right coronary artery (RCA) and the left circumflex artery (Cx) were imaged in a volume containing the artrioventricular sulcus, and the left main (LM) and the left anterior descending (LAD) were imaged in a volume containing the interventricular groove. The preferred delay time between the electrocardiogram (ECG) trigger and the mid-diastole (the period of minimal cardiac contraction) was determined from an oblique cine scout scan. The pencil-beam navigator was placed through the right hemi-diaphragm with displacements being extracted using a least-squares algorithm.

Both the prior art preparation scheme (navigator and fat saturation before preparatory RFs) and the new preparation scheme (FIG. 1) were incorporated into a navigator SSFP 3D coronary MRA pulse sequence (ECG-triggered segmented k-space balanced steady-state-free precession fast gradient echo). Presently-preferred imaging parameters were as follows: TR/TE=4.2/1.4 ms, flip angle=60°, receiver bandwidth=±62.5 kHz, 3 mm×16 slices, in-plane resolution=1.0× 1.0 mm$^2$, sequential view ordering along k$_z$, 16 partial echoes per heartbeat (corresponding to an acquisition window of 67 ms).

For navigator gating, the PAWS gating algorithm, which optimizes gating window selection and minimizes residual motion artifacts within the gating window, was implemented on a workstation that controlled data acquisition in real time. Motion bin size was 1 mm, corresponding to a gating window of 3 mm. The PAWS algorithm was optimized to insure no motion jump in the center of k-space. The most frequent motion bin was estimated from a set of navigator echoes acquired immediately prior to the current one. If this most frequent bin was assigned to acquire the edge of k-space and such acquisition had come to completion, it was then reassigned to acquire adjacent gap in k-space to avoid prolong of scan time. Three-dimensional motion was further compensated by adjusting the transmit frequency and signal reception phases according to affine motion correction algorithm.

Figure 2:
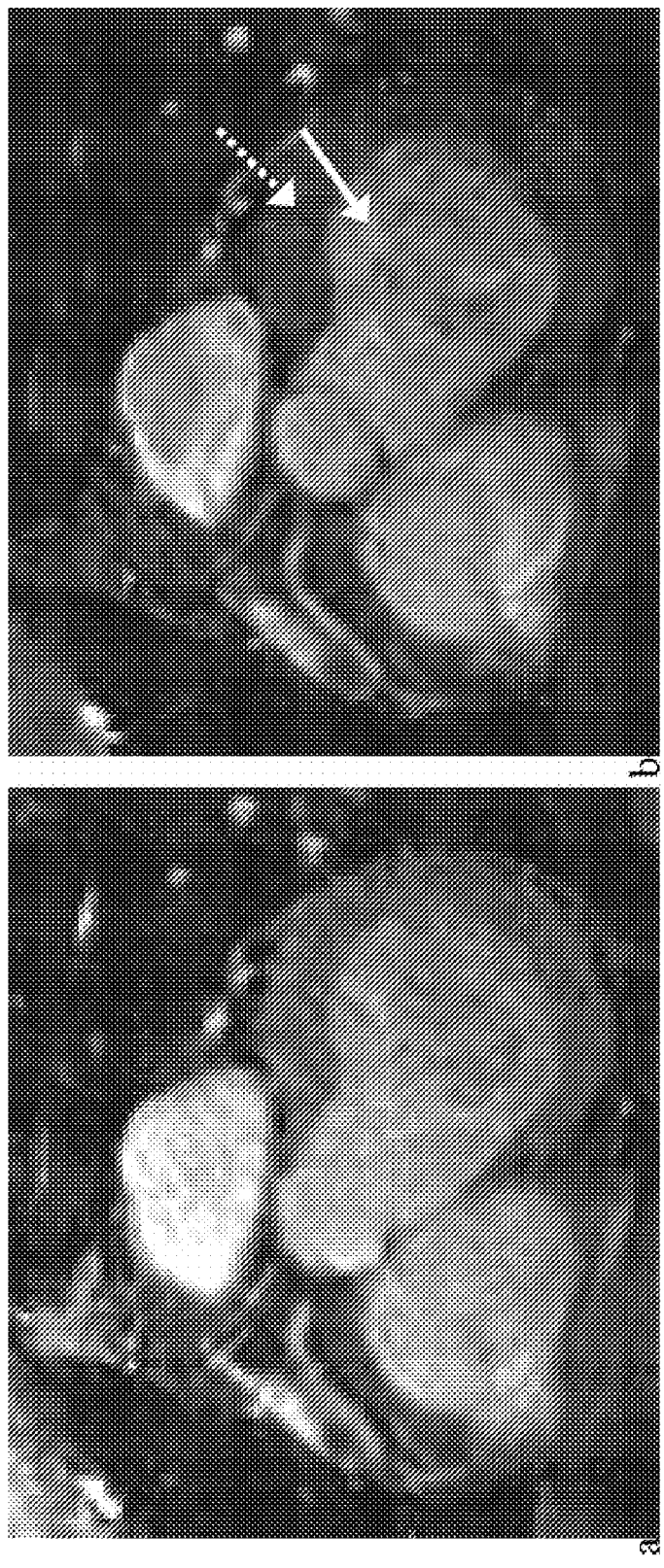
FIG. 2A displays an MRA image of RCA acquired with the prior art navigator and magnetization preparation (MP)
FIG. 2B shows an MRA image of RCA acquired in the same tissue using the navigator and magnetization preparation of the present invention.

Blood and myocardium signals ($S_{blood}$ and $S_{myocardium}$) were measured in adjacent areas of left-ventricular (LV) blood pool (solid arrow) and LV wall (dashed arrow) as indicated by in FIG. 2. FIG. 2A displays data from the prior art scheme, while FIG. 2B displays data collected using the scheme of the present invention. Sharper vessel delineation and improved blood-to-myocardium CNR are clearly observed in FIG. 2B. Fat signal ($S_{fat}$) was measured from the anterior chest wall. Noise ($\sigma_n$) was estimated from the background air above the anterior chest wall. The SNR and contrast-to-noise ratio (CNR) were defined as follows: $SNR_{blood}=S_{blood}/\sigma_n$, $SNR_{myocardium}=S_{myocardium}/\sigma_n$, $SNR_{fat}=S_{fat}/\sigma_n$, $CNR=(S_{blood}-S_{myocardium})/\sigma_n$. Two-tailed paired sample t-tests were performed to determine the statistical significance of SNR and CNR differences between the prior art scheme and the present inventive scheme. Overall image quality difference was also assessed by two independent readers: randomized image pair acquired with previous and new preparation schemes using five scales—markedly better, modestly better, approximately the same, modestly worse, and markedly worse. Paired sample signed rank Wilcoxon test was performed on the consensus image score to determine statistical significance.

The measured blood, myocardium, and fat SNR are summarized in Table 1, below. The blood-to-myocardium CNR is shown in Table 2, also below. Compared to the previous preparation scheme, the new scheme improved CNR by 46% on average (p<0.001), decreased blood SNR slightly but insignificantly by 2% on average (p=0.73), reduced fat SNR by 32% on average (p<0.001), and improved image quality (5 cases improvement, other cases similar quality; p=0.05, Wilcoxon paired sample signed rank test).

Figure 3:
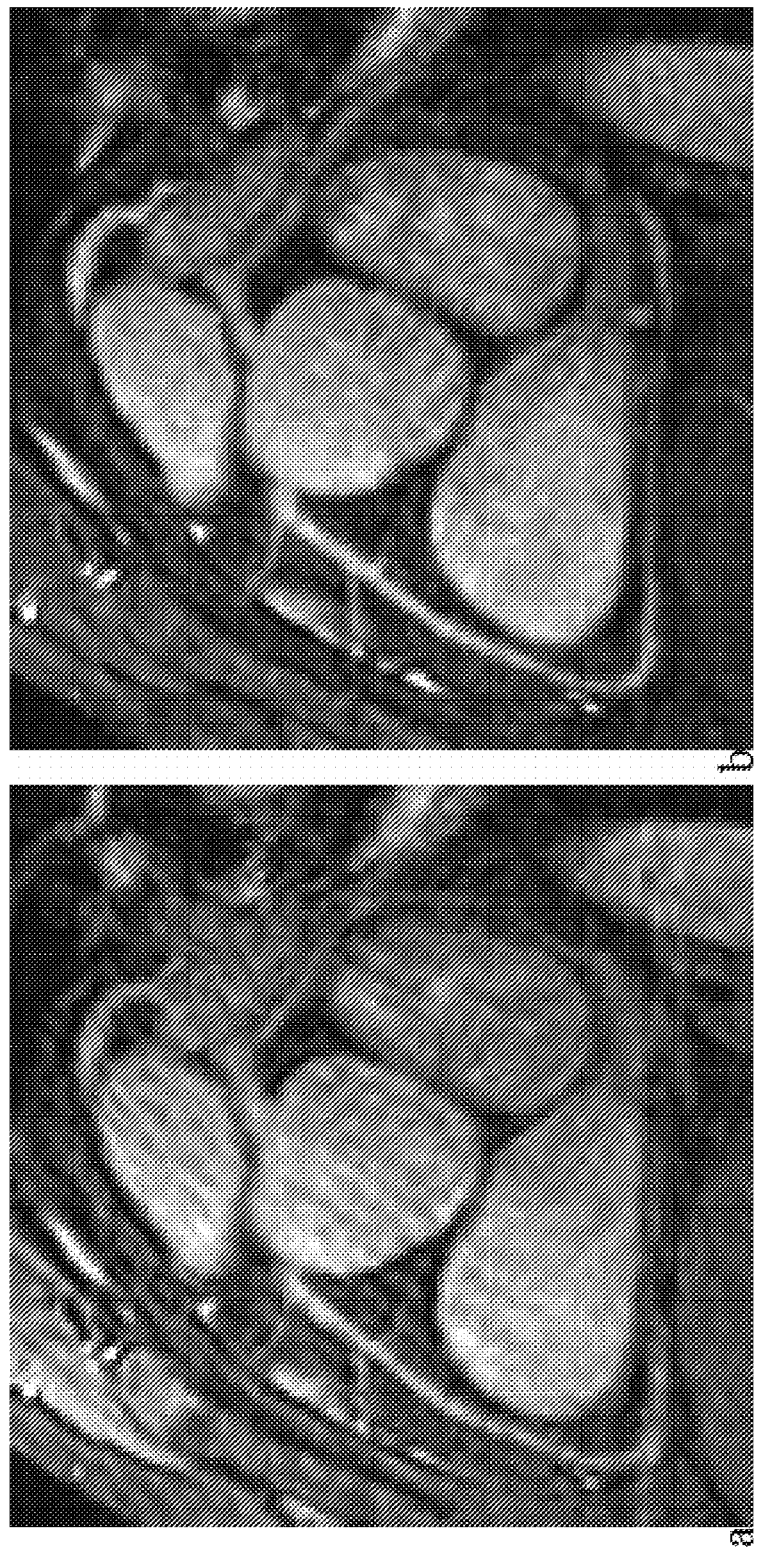
FIG. 3A displays an MRA image of RCA acquired with the prior art navigator and magnetization preparation.
FIG. 3B shows an MRA image of RCA acquired in the same tissue using the navigator and magnetization preparation of the present invention.
FIG. 3C displays an MRA image of LAD acquired with the prior art navigator and magnetization preparation.
FIG. 3D shows an MRA image of LAD acquired in the same tissue using the navigator and magnetization preparation of the present invention.
Figure 3:
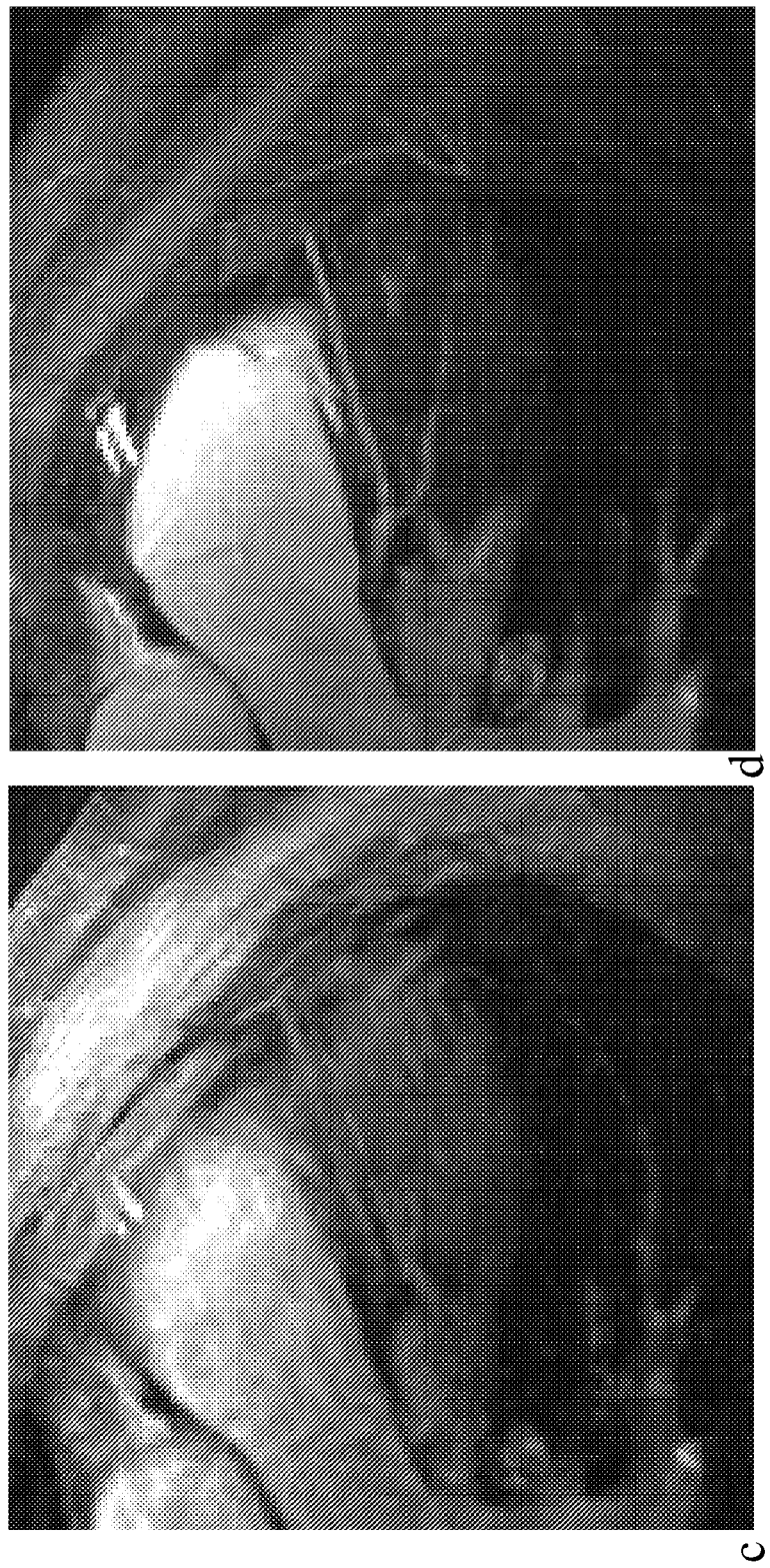

Examples of image comparison are illustrated in FIGS. 2 and 3, indicating that the new preparation scheme provided marked reduction in motion artifacts, substantial improvement in blood-to-myocardium contrast, and more effective fat suppression. FIG. 3 shows an MIP image of RCA acquired with the prior art method (FIG. 3A) and by the present invention (FIG. 3B) and MIP images of LAD acquired using the prior art method (FIG. 3C) and by the present invention (FIG. 3D).

TABLE 1

| Subject | Blood SNR | | Myocardium SNR | | Fat SNR | |
| --- | --- | --- | --- | --- | --- | --- |
| | previous | new | previous | new | previous | new |
| A | 52 | 50 | 32 | 14 | 41 | 30 |
| B | 47 | 48 | 16 | 11 | 47 | 26 |
| C | 47 | 43 | 27 | 16 | 37 | 31 |
| D | 39 | 48 | 20 | 16 | 38 | 28 |
| E | 78 | 71 | 38 | 23 | 47 | 30 |
| F | 64 | 56 | 36 | 16 | 43 | 32 |
| G | 45 | 50 | 35 | 25 | 35 | 21 |
| Mean ± SD | 53 ± 13 | 52 ± 9 | 29 ± 8 | 17 ± 5 | 41 ± 5 | 28 ± 4 |
| p | 0.73 | | 0.002 | | <0.001 | |

TABLE 2

| | Blood-to-myocardium CNR | |
| --- | --- | --- |
| Subject | previous | new |
| A | 20 | 36 |
| B | 31 | 37 |
| C | 20 | 27 |
| D | 19 | 32 |
| E | 40 | 48 |

TABLE 2-continued

| | Blood-to-myocardium CNR | |
|---|---|---|
| Subject | previous | new |
| F | 28 | 40 |
| G | 10 | 25 |
| Mean ± SD | 24 ± 10 | 35 ± 8 |
| p | <0.001 | |

The minimization of the delay between the navigator echo and the image echoes reduces the difference between the motion estimated by the navigator and the motion occurring during image acquisition. Naturally, this minimal delay is essential for effective motion suppression. This point was made by a previous study (Spuentrup, Manning, Botnar, Kissinger, Stuber. Magn. Reson. Med (2002); 47:196-201), which concluded that a 100 ms delay is problematic for high resolution navigator MRA and the delay should be reduced to 20 ms. The new scheme achieves this goal for navigator SSFP 3D coronary MRA.

Figure 4:
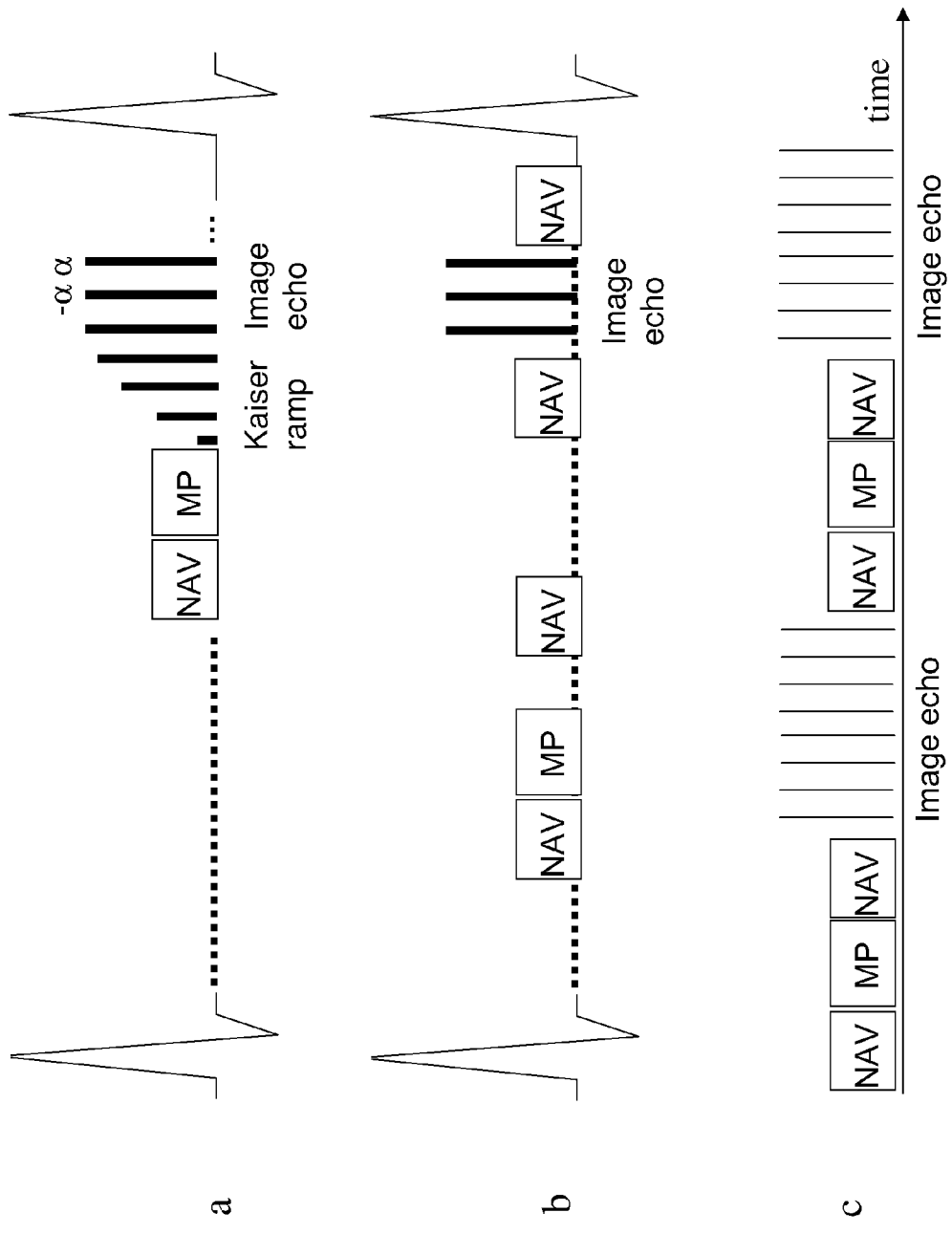
FIGS. 4A, 4B, and 4C depict additional examples of navigator (NAV) and magnetization preparation (MP) protocol of the present invention.

Additional examples of improved navigator protocol are illustrated in FIG. 4. The number of preparatory RF pulses was reduced when the amplitude of RF pulses was ramped up according to the Kaiser-Bessel function. It was found that with this Kaiser ramp, 6 RFs (in ~24 milliseconds) was enough to establish steady state, allowing sufficient accuracy in motion estimation by the navigator executed before the magnetization preparation and Kaiser ramp (FIG. 4A). When the navigator echo is from cardiac fat, then a flip angle slightly larger than 90 degree is used for the navigator to achieve simultaneous fat suppression. There may be a long delay between the magnetization preparation (MP) and image echo, such is the case with black blood imaging using inversion, the navigator echoes can be acquired multiple times through interleaving with MP and image echo (FIG. 4B). The position of the image echo can be aligned with the location of the MP using real time correction such as slice following. This improved navigator approach can be used in a general magnetization prepared segmented sequence (FIG. 4C), with the navigator (NAV) interleaved among MP and image echo.

Figures 5A, 5B:
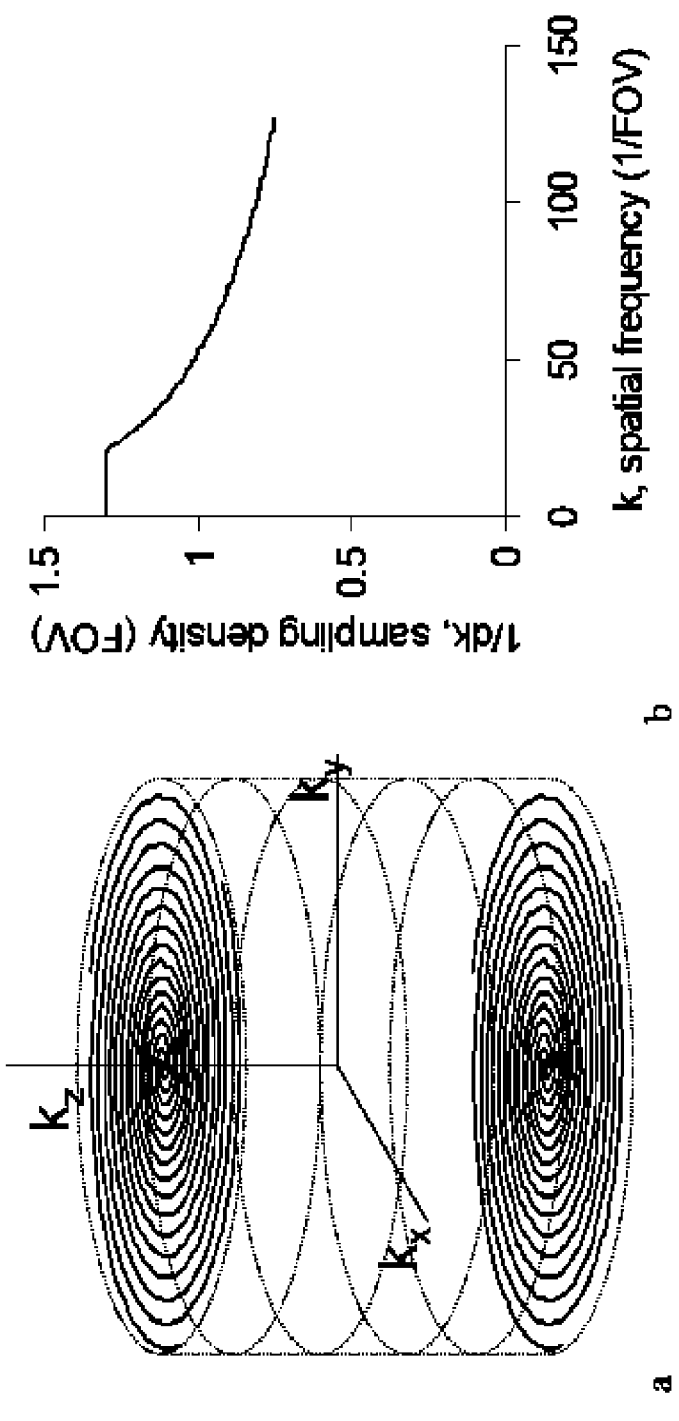
FIGS. 5A and 5B depict k-space sampling using 3D stack spiral trajectories (5A) and with a variable density (5B)
Figures 5C, 5D, 5E:
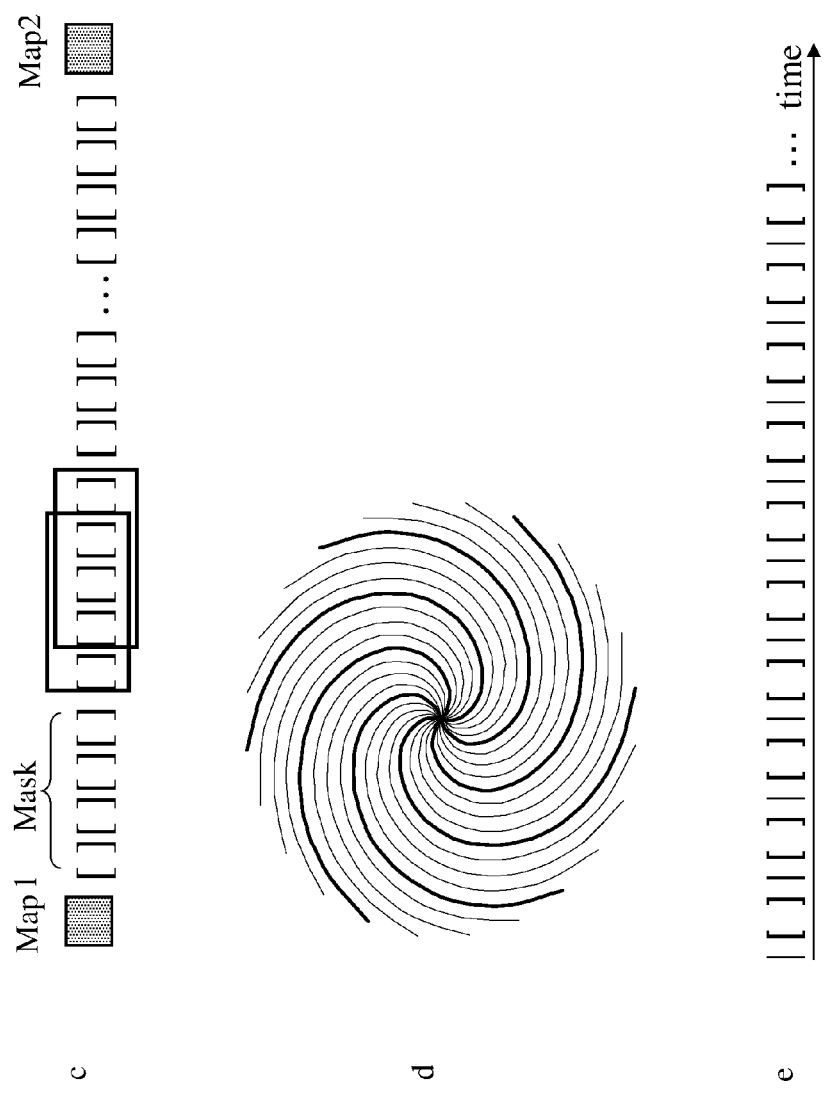
FIG. 5C shows schematics of data acquisition highlighting the inhomogeneity of field maps that were acquired at the beginning and end (grey boxes) of the sequence and the k-space sliding window (large box containing four brackets) was used for reconstruction.
FIG. 5D displays an example of one group of interleaves near the k-space center (6 thick interleaves in a full k-space of 24 interleaves)
FIG. 5E shows another example of data acquisition using time or cardiac phase resolved spiral where magnetization preparation (vertical line) is interleaved with spiral (bracket)

An additional aspect of the present invention relates to the sampling of data during MRA procedures. Specifically, the present invention provides a spiral interleaving scheme that over samples the center of k-space. A 3D stack spiral sequence was implemented with variable density as illustrated in FIG. 5. FIG. 5A displays k-space sampling using a 3D stack of spiral trajectories and FIG. 5B depicts collection using variable density. The interleaves were analytically generated to allow 30% oversampling at the center of k-space and 30% undersampling at the edge of k-space. The connection between the constant density sampling (trajectory radius linearly increasing with azimuth angle) at the center of k-space and the undersampling (trajectory radius quadratically increasing with azimuth angle) in outer k-space was conditioned to allow smooth gradient waveforms. The trajectory was uniquely determined by three parameters, the oversampling factor at the center, the transition point from constant density to variable density and the undersampling factor at the edge of k-space. View sharing and sliding window were incorporated into data acquisition and image reconstruction. Every nth interleaf of all 24 interleaves was updated sequentially as illustrated in FIGS. 5C and 5D. The updating schedule was $k_i=(n*t) \% 24+f$, here $k_i$ is the interleaf index, $t=time/(TR*N_z)$; $N_z$=number of slices; and f is the frame # with $f=[(n*t)/24]$.

For example, for n=4, interleaves of all phase encodings were updated in groups in the following order: [0,4,8,12,16,20], [1,5,9,13,17,21] ... (each bracket is represented in FIG. 5C). A complete 3D image frame was reconstructed with four consecutive groups. A new frame was reconstructed for each additional group of interleaves acquired. Thus, the frame time was one nth of the scan time for a full k-space data set. This study utilized interleave schedules of n=4 and 6. A complete set of k-space data acquired prior to contrast arrival was used for mask subtraction performed as a complex subtraction in k-space.

The spiral imaging sequence can be applied to general time resolved imaging as illustrated in FIG. 5E. The spiral trajectory can be generalized a larger class of non-linear lines in k-space. Magnetization preparation along with appropriate view ordering can be used to generate desired contrast. For example, the cardiac phased resolved imaging can be implemented with this sliding window spiral approach to study the anatomy and function of the heart. The image echo can be either spin echo type for black blood imaging, or gradient echo type for bright blood imaging. Data can be interpolated to account for variation in the cardiac cycle to generate cine movies of the heart.

The frequency segmented off-resonance correction with field maps was implemented using 10 bins over the whole frequency range (100-200 Hz). For the present study, an initial first field map was acquired at the beginning of the scan and was used to correct the first half of temporal frames. A second field map was acquired at the end of the scan for correcting the remaining frames. For comparison, the prior art off-resonance correction based on minimizing the imaginary part of the image signal (after compensating for a constant phase offset associated with the data in the k-space center) was also implemented.

In vivo studies were performed on 5 healthy subjects and 12 medical patients. Five to eight milliliters of gadopentetate dimeglumine was injected at 1-2 cc/sec in all studies. Arteries in the calves and the Circle of Willis were imaged with a standard head coil on a 1.5 Tesla MR scanner. Other anatomical regions were imaged utilizing a body coil. Imaging parameters were: 24 spiral interleaves in $k_x k_y$ plane, 2640 points per interleaf, 32 $k_z$ slice encoding, 30-36 cm FOV, 1-3 mm slice thickness, 256×256 matrix recon matrix, 1.1/11.7 msec TE/TR, 60° flip angle, and the receiver bandwidth was 200 kHz using the head or body coil. The scan time was 5.6-8.9 second (62.5-100% $k_z$). Field mapping parameters were: 32×32 matrices, 1.1 and 3.1 msec TE, 15 and 17 msec TR, 4 interleaves, 2256 points per interleaf, same $k_z$ and slice thickness and FOV as imaging, and 3 second scan time per map. Data were acquired for 40-60 seconds.

Figure 6:
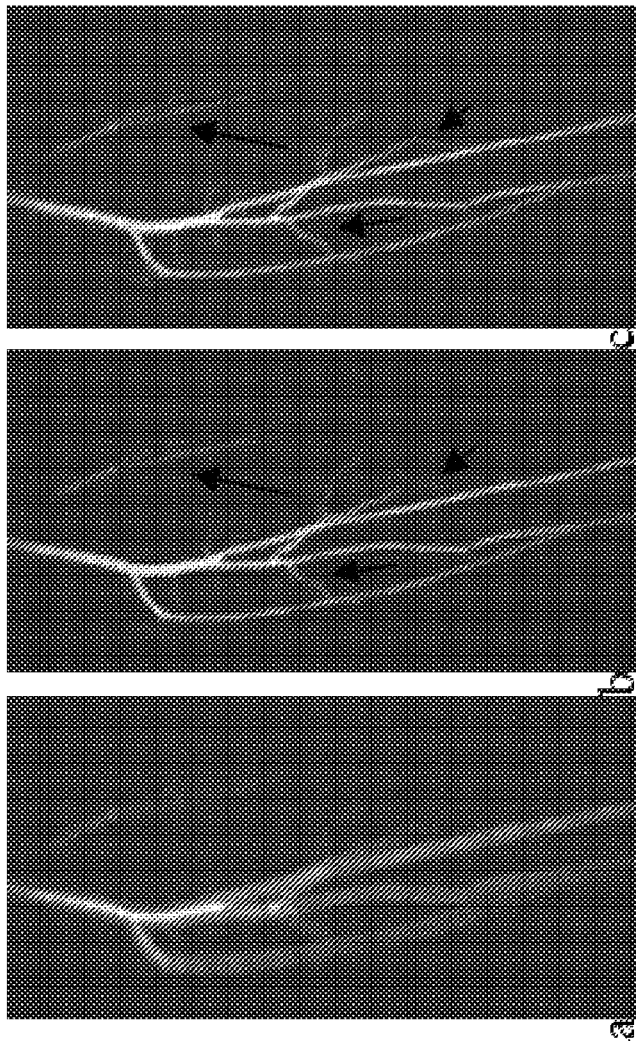
FIGS. 6A, 6B, and 6C show an anteroposterior image (MIP reconstruction) without inhomogeneity correction (6A), with correction using the imaginary-minimization method (6B), and corrected with an acquired field map according to the present invention (6C) with arrows showing areas of marked improvement.

The off-resonance correction is illustrated in FIG. 6. There was substantial blurring without off-resonance correction (FIG. 6A). The correction based on imaginary minimization reduced blurring substantially (FIG. 6B). The correction based on the acquired inhomogeneity field maps further improved the delineation of small vessels (arrows in FIG. 6C), which was consistently observed in 5 consecutive cases (p=0.05, paired sample signed rank Wilcoxon test). Furthermore, the field map correction was 5 times faster than the imaginary minimization correction.

Figure 7:
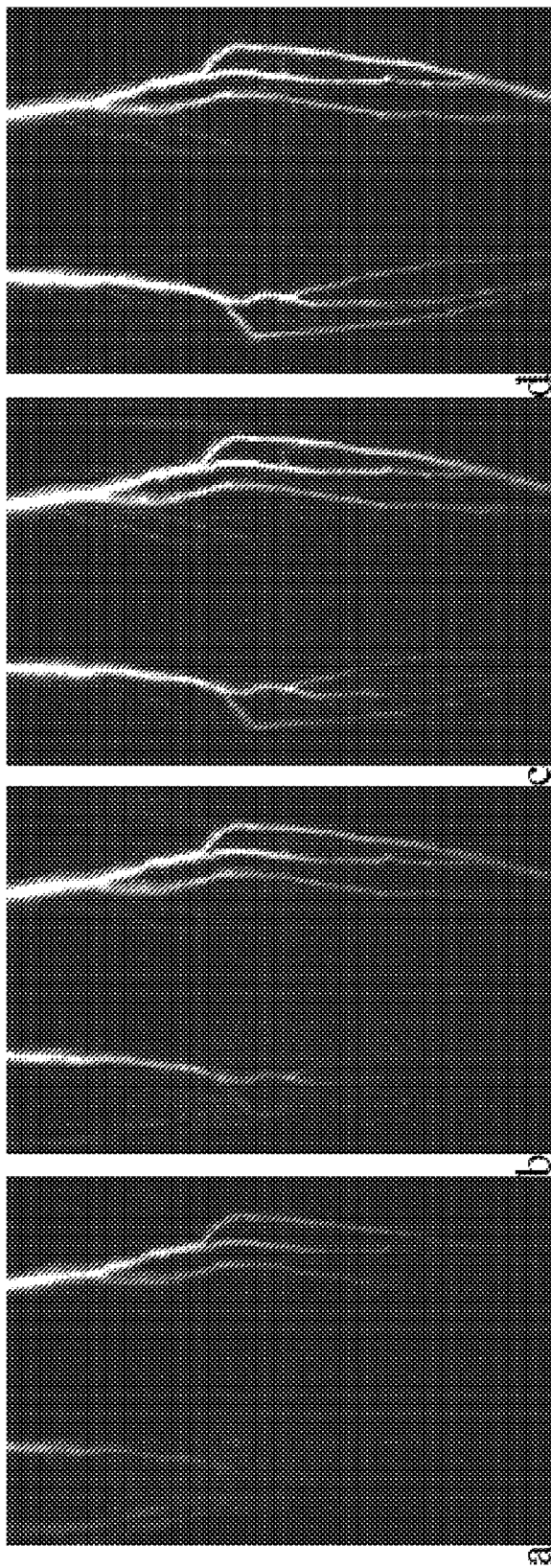
FIGS. 7A, 7B, 7C, and 7D display four consecutive frames (frontal MIP, 2 seconds/frame) from a normal volunteer demonstrating the time resolved capabilities of the spiral data collection method of the present invention.

High quality 3D spiral MRA at 1-2 second frame rate was obtained in all subjects and patients. Typical examples are shown in FIGS. 7-11. FIG. 7 illustrates a patient with 4 consecutive frames (at 2 seconds per frame) depicting asymmetrical filling of the tibial trifurcations (approximately 4 second delay in the right calf). FIGS. 7A-7D are four consecutive frames (frontal MIP, 2 seconds/frame) acquired in a patient. Those images demonstrate the time-resolved capabilities of the spiral method of the present invention. Contrast arrived at the right tibial trifurcation after a delay of approximately 4 seconds.

Figure 8:
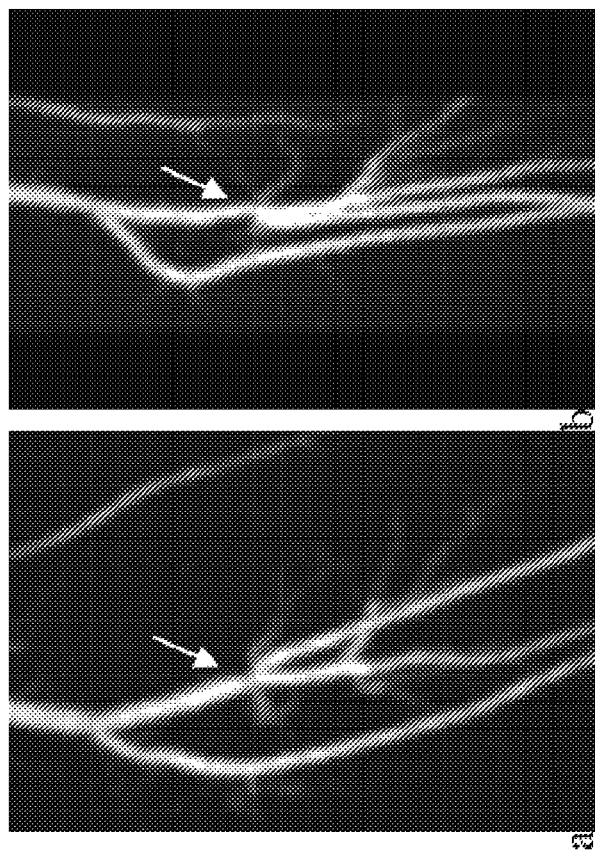
FIGS. 8A and 8B show a frontal (8A) and lateral (8B) MIP from the peak frame acquired from a patient with an arrow indicating an eccentric compression of the distal tibioperoneal trunk.

FIG. 8 illustrates a patient with 2 different views of the same vessel delineating an eccentric lumen. FIG. 8A displays a frontal MIP from the peak frame acquired in a patient, while FIG. 8B depicts a lateral MIP. The difference in vessel diameter between the two projections depicts an eccentric compression of the distal tibioperoneal trunk, as indicated by the arrows.

Figure 9:
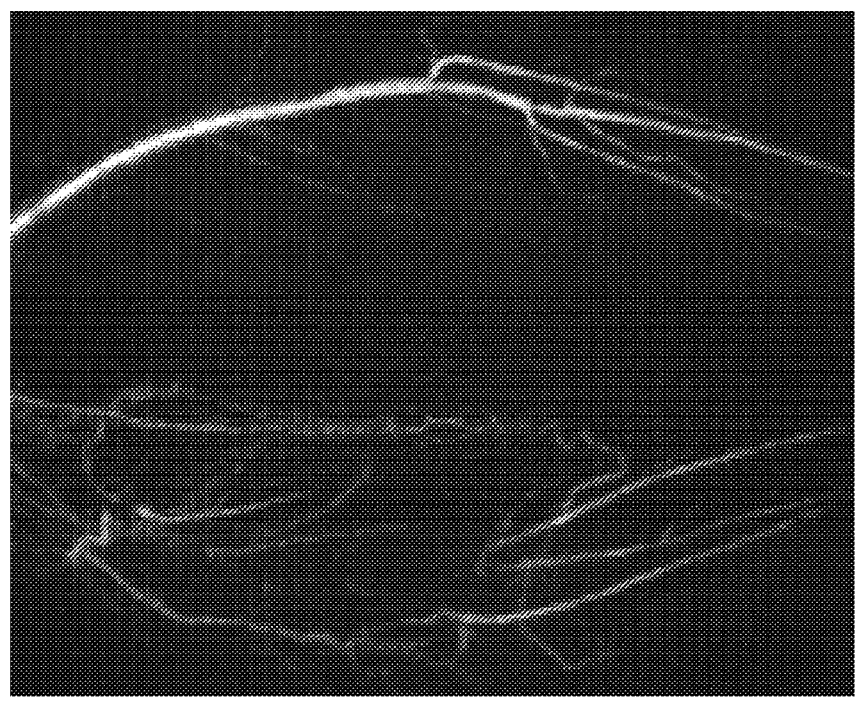
FIG. 9 displays a frontal MIP construction at peak arterial phase enhancement from a clinical patient demonstrating occlusion of the distal right superficial femoral artery and the popliteal artery with reconstruction of the proximal anterior tibial, peroneal, and posterior tibial arteries.
Figure 10:
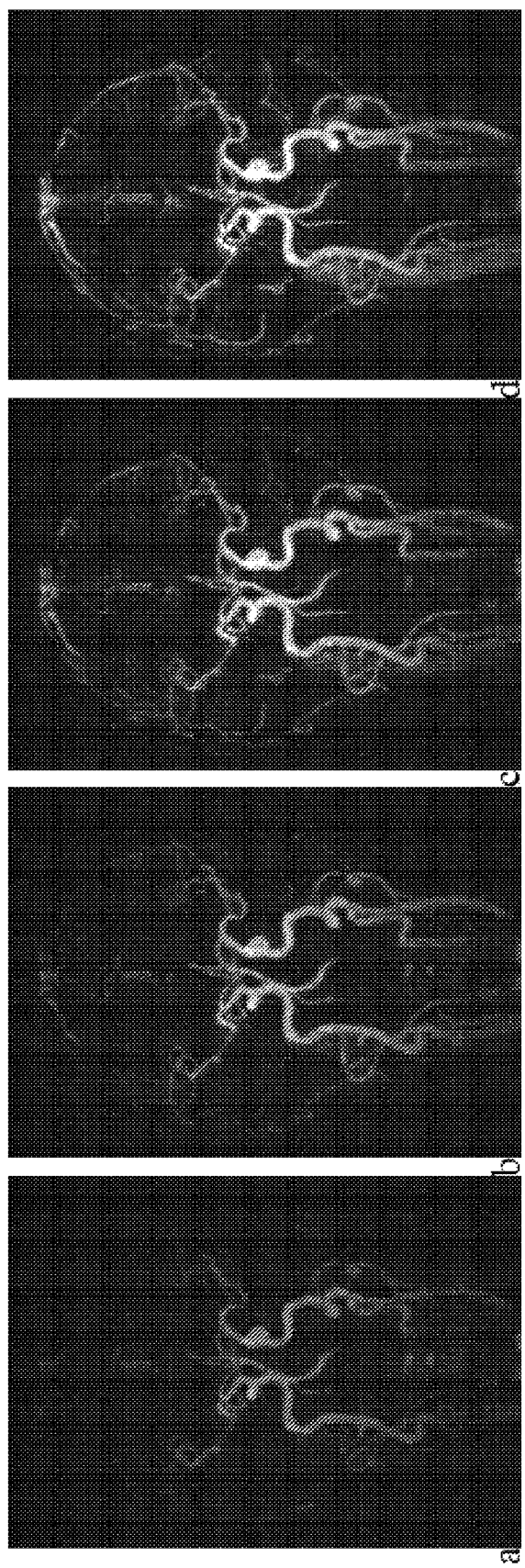
FIGS. 10A, 10B, 10C, and 10D show time-resolved 3D MRA of the neck and head acquired at 1 frame per second using 5 cc Gd injected at 1 cc/second showing contrast bolus circulation from carotid arteries to the Circle of Willis, cerebral branch arteries, saggital sinus, and the jugular vein.

FIG. 9 illustrates a patient case of long occlusion in the right superior femoral and popliteal arteries. An example of time resolved 3D spiral MRA of the carotid arteries and cerebral arteries is demonstrated in FIG. 10, acquired at 1 second per frame using a head coil. FIGS. 10A-10D display four consecutive frames and demonstrate the temporal resolution of the techniques of the present invention. The bolus circulation time from the Circle of Willis to the saggital sinus was approximately 2 seconds. Another example of time resolved 3D spiral MRA of the thoracoabdominal arteries is demonstrated in FIGS. 11A-C which are sequential frames acquired at 2 seconds per frame using a body coil. The dynamics of renal parenchymal enhancement were visualized from the collected time resolved images.

It should be emphasized that the additional vessel enhancement between two adjacent frames is captured without visible artifacts (FIG. 7). This implies that a highly undersampled k-space represented by one group of interleaves in FIG. 5 is sufficient for imaging a vascular tree sparsely distributed in image space. The vast dark background has insufficient signal intensity to generate severe artifacts in reconstruction of the undersampled k-space data. Sliding window reconstruction generates a frame time much less than the sliding window duration or the scan time for a full k-space data set.

The time resolved 3D spiral MRA technique is presented here as a means to add adequate temporal resolution to current 3D contrast enhanced MRA. This work can also be regarded as an extension of the previous 2D MR fluoroscopy work by adding the depth resolution. The lengthy reconstruction time may forbid real time display of time resolved 3D spiral in general. For updating local changes in the catheter position, a small FOV and a small amount of data may be sufficient. In this situation, off-resonance correction may not be necessary and the reconstruction time may be vastly reduced. Accordingly, real time visualization of 3D motion of a catheter in a vessel tunnel during intervention may be possible using this time resolved 3D spiral technique.

The higher SNR efficiency of the spiral sampling over the radial sampling can be established using the standard voxel SNR equation applied to the spoiled gradient echo sequence. This may also be explained in the following intuitive manner. The sampling time provides double values for both longitudinal magnetization regrowth and data sampling, therefore should be prolonged as long as allowed by T2* decay. Enhanced blood T2* is on the order of 10 msec. Spiral trajectories allow sampling for a long time, while the straight radial trajectories only allow ~1 msec sampling time at the same receiver bandwidth. Accordingly, the spiral sampling is faster and more SNR efficient than the radial sampling.

The technique implemented in this preliminary study can be further refined and improved in many aspects, particularly in data processing. The off resonance correction may be further improved by estimating the inhomogeneity field associated with the contrast bolus according to the phase evolution in the time resolved data. The more concerning practical issue is image reconstruction time, which was about an hour on a current standard single processor (400 MHz MIPS R12000, SGI), because each 3D volume had to be reconstructed repetitively 90 times: 10 resonance frequencies and 9 time resolved phases in the preliminary study. Higher data matrix and multi-coil data acquisition would substantially increase the reconstruction time. The reconstruction may be accelerated with parallel computing over multiple processors. A UNIX computer cluster of 8 processors were tested for image reconstruction. Each processor reconstructs one volume, allowing 8 image volumes to be reconstructed simultaneously to shorten scan time by 8 fold. More processors and better parallelization of the computation task can be used to achieve real time reconstruction for time resolved 3D spiral imaging with multiple RF coils.

Figure 12A:
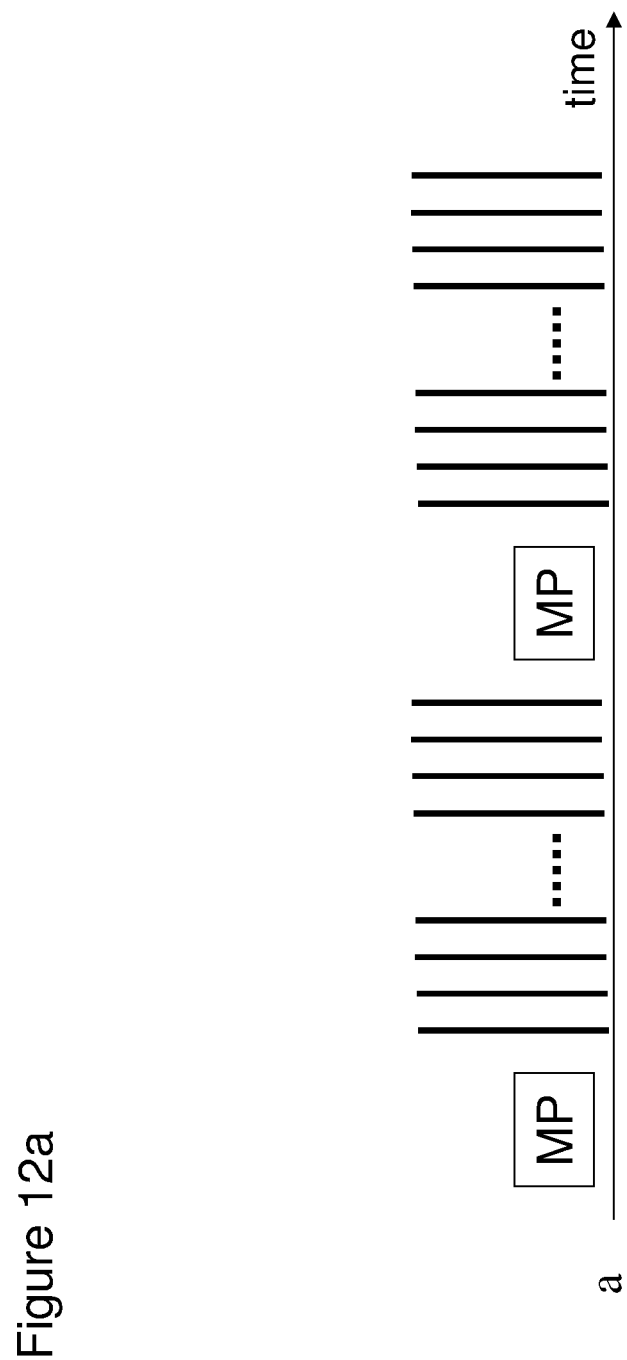
FIG. 12A shows a protocol of magnetization prepared segmented magnetic resonance imaging.

In an additional aspect of the present invention, view ordering to maximize image contrast and minimize image artifacts in magnetization prepared MRI (FIG. 12A) was evaluated in further SSFP experiments. Specifically, view ordering schema were developed that allow for maximal image contrast and minimal artifacts associated with eddy currents in MP SSFP imaging. Inversion was used to null background, and SSFP acquisition was used to capture the contrast bolus in the arteries for generation of MRA.

Figures 12, 12B, 12C:
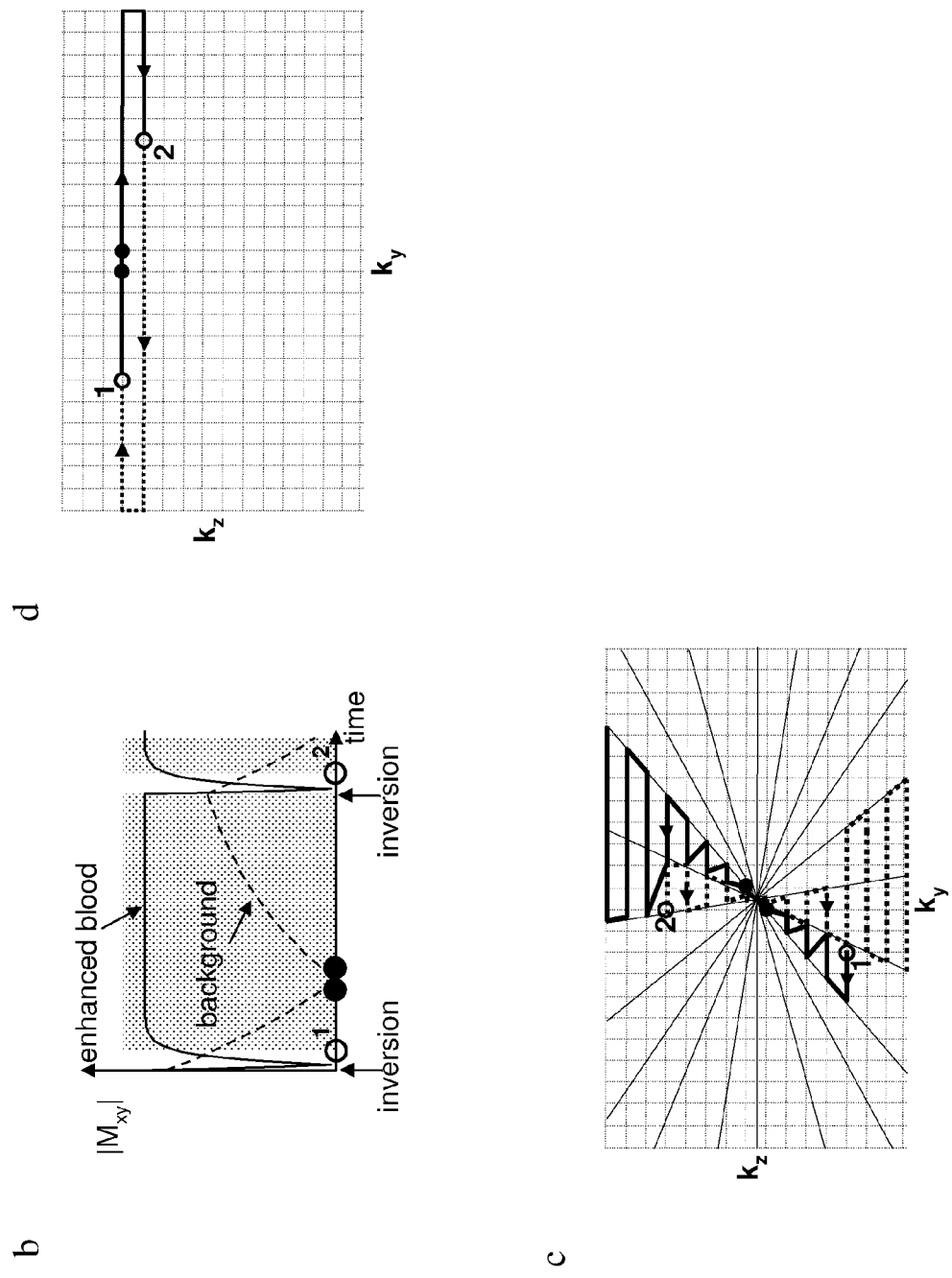
FIG. 12B shows the time course of background and contrast signal in an CERMA application of the present invention.
FIG. 12C displays data acquisition according to the present invention using a fan order trajectory where $k_y k_z$-space is divided into radial fans (i.e., wedges), each containing a segment of views acquired between two adjacent inversions.

The signal evolution in an inversion prepared SSFP sequence is illustrated in FIG. 12B for both enhanced blood and background. The inversion pulse is accompanied by $\alpha/2$ pulses to smooth the transition to the steady state. Theoretical considerations showed that this magnetization preparation provides an oscillation-free recovery after inversion for a wide range of off-resonances. After each inversion pulse, $N_{disdacq}$ disdacqs are applied to allow the contrast enhanced blood signal to recover to its steady state value. Then data acquisition proceeds to collect a segment of views ($N_{dacq}$=number of views with data acquisition enabled (dacq) per segment; $N_{seg}$=number of segments; and $N_{dacq}*N_{seg}$=total number of views). The total number of RFs ($N_{disdacq}+N_{dacq}$) following each inversion pulse is such that the background signal level does not exceed a certain threshold. Because the background signal varies throughout the data collection duration, the central portions of k-space should be acquired at the background signal nulling points. Because of the sensitivity of SSFP imaging to changes in eddy currents associated with phase encoding gradients, it is preferable to follow a smooth trajectory in $k_y k_z$-space.

Two view orders that satisfy the above criteria are illustrated in FIGS. 12C and 12D, which will be referenced herein as fan order and loop order, respectively. In the fan order (FIG. 12C), the $k_y k_z$-space is divided into radial fans, each containing $N_{dacq}$ views and consisting of two diametrically opposed sections. Each fan is sampled following an edge-center-edge trajectory with a zigzag pattern to minimize gradient changes between successive views. The first view within a fan (empty circle in FIG. 12) is such that the center region of the fan (solid circles in FIG. 12) is traversed at the background nulling point. Consequently, a number of views near the edge of $k_y k_z$-space in the starting section of the fan are skipped. To make up for these skipped views, the trajectory includes views from an adjacent fan as it approaches the edge of $k_y k_z$-space in the second section. By repeating this procedure for consecutive fans, a full set of k-space data is acquired. In the loop order (FIG. 12D), lines of constant slice encoding $k_z$ are acquired successively. Similar to the fan order, the first view for each $k_z$ line is chosen such that the acquisition of the central $k_y$ views occurs at minimal background signal. The skipped views are acquired at the end of the next $k_z$ line (see FIG. 12D). Here $N_{dacq}$ is necessarily equal to a multiple of the total number of phase encodings. The schematics illustrated in FIG. 12D can be modified to sample multiple $k_z$ points before advancing to the next $k_y$. This loop order has the advantage of allowing the slice encoding ($k_z$) ordering to be matched to the blood enhancement time course.

An SSFP pulse sequence with the magnetization preparation and the view ordering schemes shown in FIG. 12 was implemented on a 1.5 Tesla scanner. The pulse sequence calculated $N_{dacq}$ and $N_{disdacq}$ based on the prescribed minimal enhanced blood signal, the maximal background signal (both measured with respect to their steady state values) and their assumed relaxation times. For comparison, two additional view ordering schemes were included in our experiments: 1) the standard sequential view ordering, modified to acquire successive lines of constant phase encoding in opposite directions—satisfying only the smooth trajectory criterion; and 2) the segmented recessed centric view ordering, in which the views were first arranged into a recessed centric ordered sequence, then assigned sequentially to each segment one view at a time, with the assignment repeated until all views are exhausted—satisfying only the minimal background criterion. Such a segmented recessed centric view order is similar to the fan order but without the smooth k-space trajectory.

To compare the different view orderings, eight uniform gelatin phantoms with different concentrations of Gadolinium (Gd) were studied. One phantom (T1/T2=1060/405 ms) represented background tissue, a second (T1/T2=58/42 ms) corresponded to contrast enhanced blood, while the other phantoms were included for reference. Using these relaxation times, a minimal enhanced blood signal regrowth of 85% and a maximal background signal regrowth of 85%, the pulse sequence played out 33 disdacqs and 430 dacqs after each inversion, or a total of 463 TRs between two consecutive inversions. The experiment was repeated using a maximal background signal regrowth of 60%, resulting in 33 disdacqs and 222 dacqs. In both experiments, however, the number of dacqs for the segmented recessed centric view ordering remained the same (256=number of phase encodings). Scanning parameters were TR/TE=4.1 ms/1.3 ms, flip angle=60°, rbw=±62.5 kHz, FOV=30 cm, 3 mm slice thickness and a 256×256×16 acquisition matrix. Total scan time was 18 seconds (standard SSFP), 19 seconds (430 dacqs), and 20 seconds (222 dacqs). Background SNR was measured to assess the effectiveness of the background suppression. The SNR standard deviation (std dev) in a uniform ROI was measured to assess the eddy current artifacts.

An animal study using an intravascular contrast agent was also performed using two Yorkshire swine (30-45 kg). Each animal was sedated with an intramuscular injection of ketamine (20 mg/kg body weight) and xylazine (2 mg/kg body weight), then induced with a sodium thiopental (20 mg/kg body weight) IV, intubated and maintained on a 1.0-3.0% isoflurane and oxygen inhalational anesthesia with mechanical ventilation for the duration of the study. The assumed relaxation times were T1/T2=50/30 ms for contrast enhanced blood (0.1 mmol/kg dose, MRA acquired immediately after injection) and 1000/100 ms for background tissue, resulting in $N_{disdacq}$=26 and $N_{dacq}$=160 for an 85% maximal background signal regrowth. The view ordering that delivered maximal background signal suppression in the phantom experiments was used. Scanning parameters were TR/TE=4.2 ms/1.4 ms, flip angle=60°, readout bandwidth=±62.5 kHz, coronal FOV=26 cm, 2.4 mm slice thickness and a 256×256×48 acquisition matrix. Total scan time was 43 seconds. The volume contained the heart, pulmonary vessels and aorta.

Figure 13:
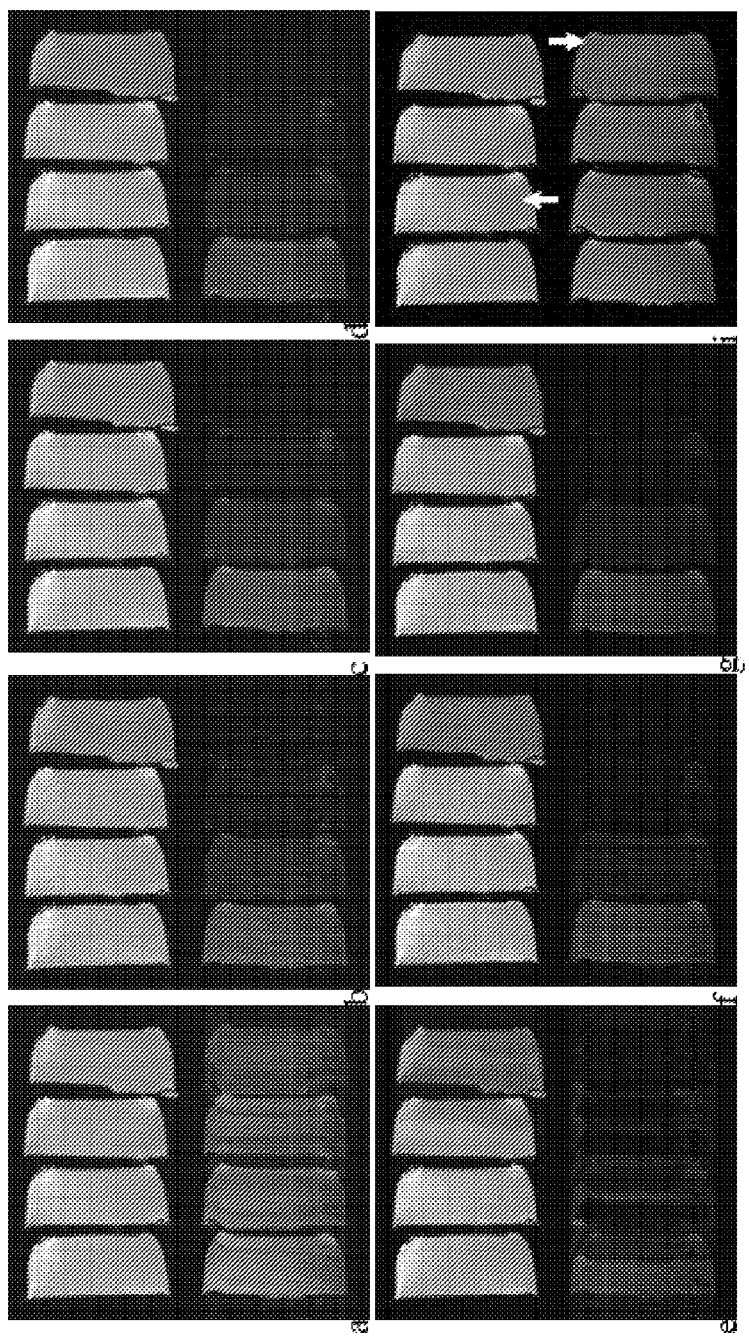
FIGS. 13A-13I display comparisons of different view ordering schemes with 13A and 13E being prior art, sequential; 13B and 13F being segmented recessed centric; 13C and 13G using the fan order of the present invention; 13D using the loop order of the present invention; and 13I using standard SSFP (no magnetization preparation) with white arrows indicating "background" and "enhanced blood" phantoms.
Figure 14:
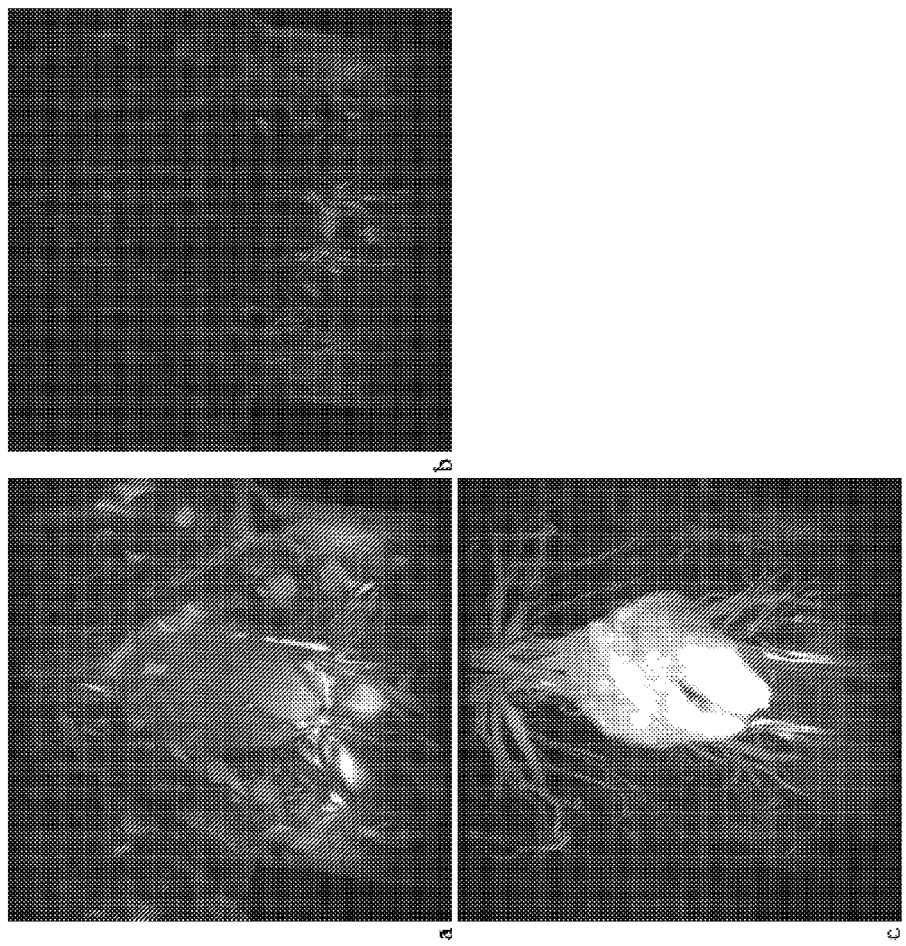
FIGS. 14A, 14B, and 14C show SSFP MIP images of pig thorax using pre-contrast without inversion preparation (14A), precontrast with inversion preparation using fan order scheme of the present invention (14B), same as (14B) but immediately after an injection (14C)
Figure 15:
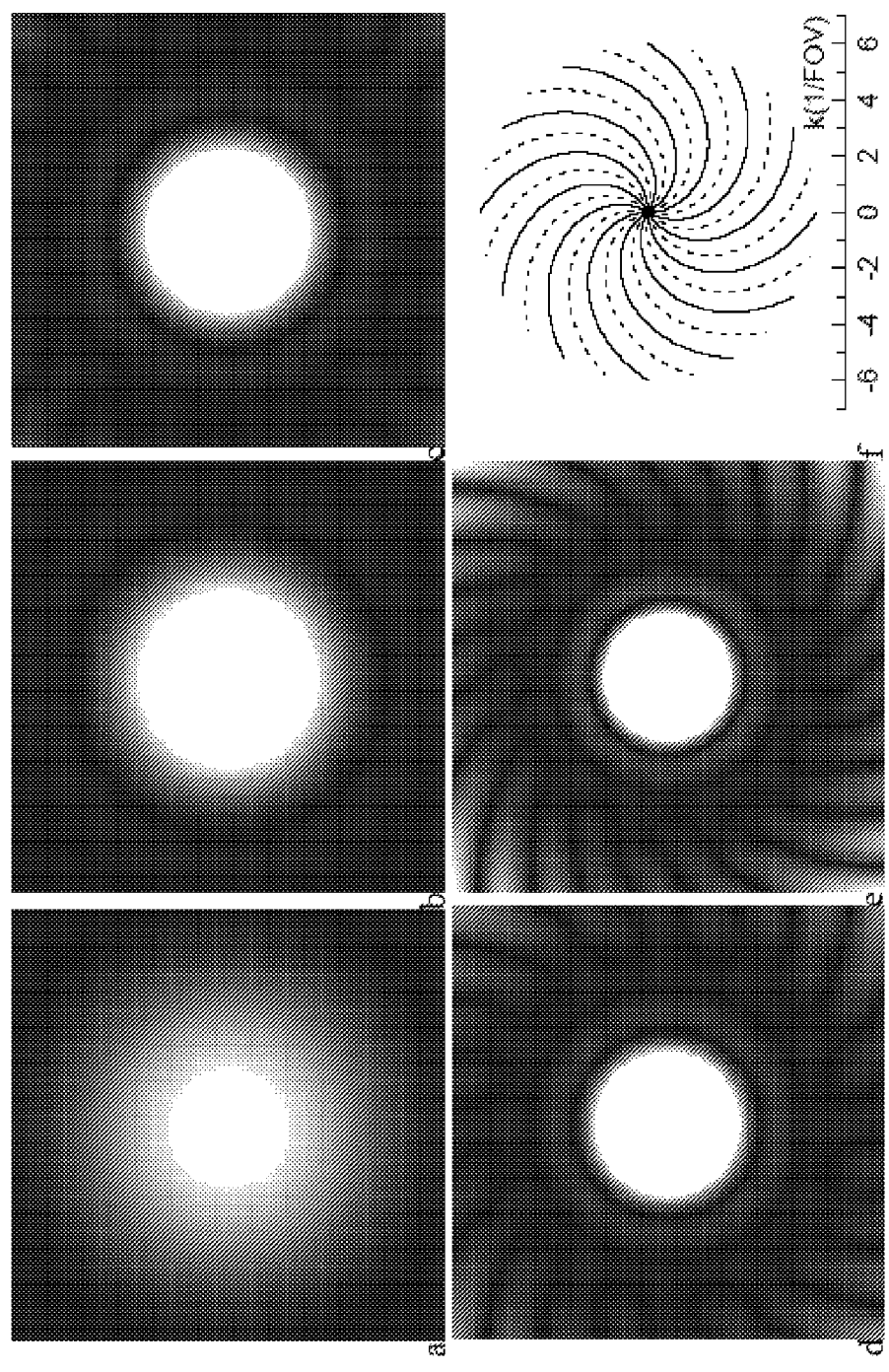
FIGS. 15A-E represent low-resolution PSFs of 2× undersampled data in central regions of k-space in central regions of k-space with radii (15A) 2/FOV, (15B) 3/FOV, (15C) 4/FOV, (15D) 5/FOV, and (15E) 6/FOV.
FIG. 15F displays the 2× undersampling with the solid lines being data collected and dashed lines being skipped data.
Figure 16:
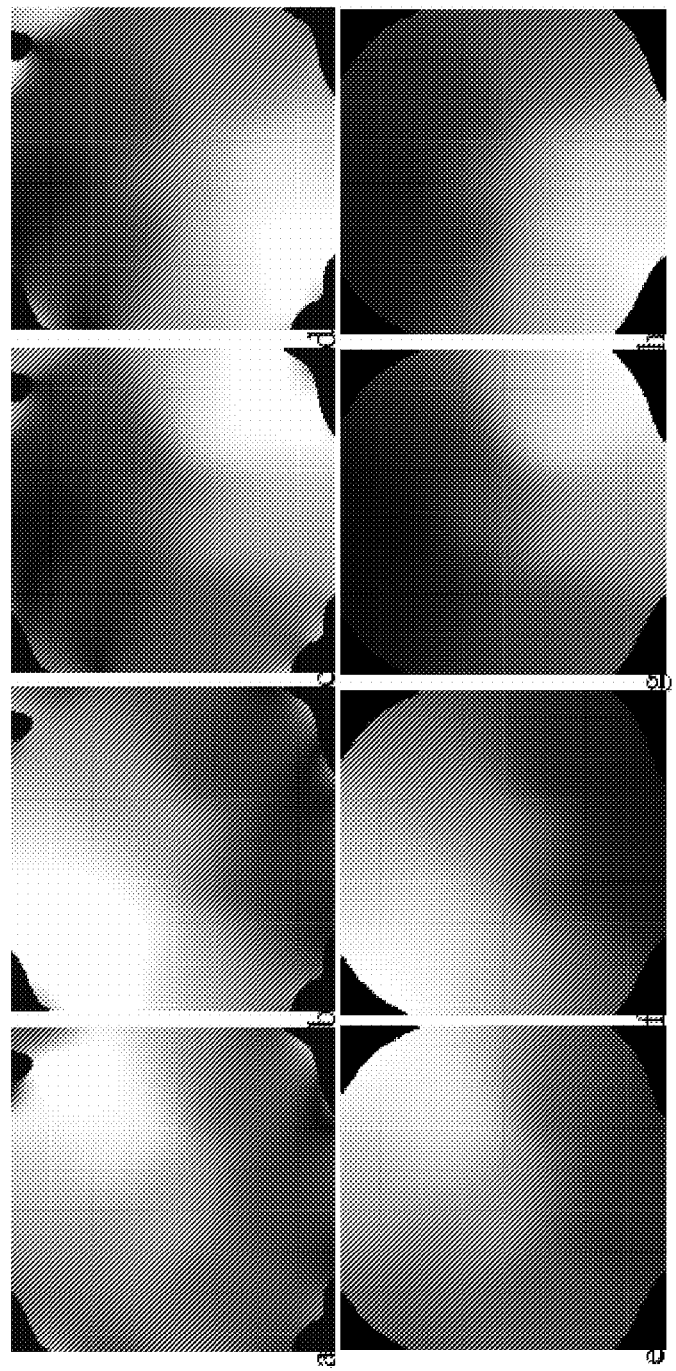
FIGS. 16A-H show normalized low-resolution images from 4 different coil elements obtained from the 2× undersampled data in a k-space center of radius 4/FOV (16A-D) and corresponding normalized low resolution images from fully-sampled data (16E-H)

Phantom experiments comparing view orders are summarized in FIG. 13 and Table 3. The prior art sequential view order led to a fair amount of background signal reduction (35% at $N_{dacq}$=430) at the cost of substantial artifacts (FIGS. 13A and 13E, 15 SNR std dev at $N_{dacq}$=430 in the first column of Table 3). The segmented recessed centric view order improved the background reduction (90% at $N_{dacq}$=430) with reduced but still marked image artifacts (FIGS. 13B and 13F, 8 SNR std dev in the second column of Table 3). The fan order scheme maintained a good reduction of background signal (94% at $N_{dacq}$=430) while at the same time reducing image artifacts (FIGS. 13C and 13G, 3 SNR std dev in the third column of Table 3). The loop order scheme led to a similar background SNR reduction (91%) with comparable artifact suppression (FIG. 13D), 3 SNR std dev in the third column of Table 3). FIG. 13I displays data from a standard SSFP with no magnetization preparation. The arrows in FIG. 13I indicates "background" and "enhanced blood" phantoms. Except for the prior art sequential view order, the increase in inversion frequency from $N_{dacq}$=430 to $N_{dacq}$=222 (corresponding to an increase in scan time from 19 seconds to 20 seconds) only marginally improved background suppression (FIG. 13 and Table 3). The fan view order that provided the best background suppression in the phantom experiment was used in pig experiments. Substantial suppression of background tissue was observed (FIGS. 14A and 14B). Angiograms from an inversion prepared SSFP acquisition without background subtraction were obtained immediately after contrast injection (FIG. 14C), demonstrating contrast enhanced heart, aortic arch, subclavian vessels, aorta and pulmonary vessels.

TABLE 3

| | Inversion prepared SSFP | | | | |
|---|---|---|---|---|---|
| $N_{dacq}$ | Standard sequential order | Segmented recessed centric order | Fan order | Loop order | SSFP |
| 222 | 14.3 ± 7 | 13.0 ± 3 | 8.2 ± 3 | 12.6 ± 3 | 136.3 ± 12 |
| 430 | 88.5 ± 15 | 13.1 ± 8 | 8.4 ± 3 | N/A | |

The view order design described in this paper may be generally applicable to most magnetization preparations, including the inversion preparation discussed here and fat suppression. Both the fan and loop order introduced minimal changes in the phase/slice encoding gradients leading to minimal eddy current artifacts (typically ringing in images). The fan order provided a slightly better background suppression than the loop order. This might be explained by the fact that, in the fan order, the k-space center is better matched to minimal background signal, enhancing signal contrast.

Several variations of the fan order are possible. For example, a segment of views could consist of two sections that are adjacent instead of diametrically opposed. When the trajectory approaches the k-space edge in the second section of the fan, it can include extra views from either of the two neighboring fans. In the present scheme, the trajectory advances to a new fan; in an alternate scheme, the trajectory can advance to a visited neighboring fan. With an optional special fan for residual views, any set of fans of desired size can form a compact covering of k-space. Accordingly, the implementation of the fan order can be adapted to any imaging matrix. It is likely that the fan order may be the method of choice for many magnetization prepared SSFP acquisitions. In the implementation of the loop order, the number of views acquired per segment has to be an integer multiple of the phase encodes ($N_y$). Accordingly, the highest magnetization preparation frequency in the loop order scheme occurs when $N_{dacq}$=$N_y$, which may be sufficient for most magnetization preparations. Aside from being straightforward to implement, the loop order has the additional advantage of allowing $k_z$ collection to be matched to the contrast bolus time course, which may be beneficial for first pass contrast enhanced MRA. The fan order, on the other hand, returns to the $k_y k_z$-space center throughout the whole scan. In a more advanced approach, $k_y k_z$-space could be divided into a central and a peripheral region before it is further divided into fans. Subsequently, fans containing the views closest to the $k_y k_z$-space origin would be placed around the expected peak enhancement. In this case, a balance would have to be struck between two opposite requirements: 1) to spread out the acquisition of central $k_y k_z$-space views over all background nulling points; and 2) to group the acquisition of those central views to match the bolus time course. By repeatedly going back near the center of $k_y k_z$-space, the fan order offers the possibility of navigation or motion tracking during the scan. In the present implementation, however, every view is acquired only once. Additional echoes may be acquired during disdacqs and used to extract motion between segments.

In an additional aspect of the present invention, a method is employed that improves the prior art MRI applications. In particular, a spiral SENSE scheme is employed to collect data for MRI applications.

The spiral SENSE algorithm using conjugate gradient iteration requires the input of normalized coil sensitivity maps, $C_l(r)/(\Sigma_l |C_l(r)|^2)^{1/2}$. In the prior art SENSE implementation, the normalized coil sensitivity maps are estimated from the fully sampled low resolution reference scan with normalization: $L_l(r)/(\Sigma_l |L_l(r)|^2)^{1/2}$. For the self-calibration of the present invention, the reference scans are replaced with k-space center data in the accelerated acquisition itself. For more accurate coil sensitivity estimation, the spatial resolution is desired to be sufficiently high to contain all major spatial frequencies of coil sensitivity; but at such spatial resolution, there are substantial undersampling artifacts.

The size of the k-space center is preferably selected by balancing between the spatial details for coil sensitivity maps and the amount of residual artifacts from undersampling. In the spiral sampling trajectory of the present invention, the sampling density is above the Nyquist limit in the very center of k-space, and then diminishes below the Nyquist limit as data sampling moves away from the center. As the radius of k-space data used in reconstructing the low resolution images increases, image resolution increases (allowing more detailed estimation of coil sensitivity) but artifacts from undersampling start to appear and increase. Data are densely sampled along the interleaves in spiral trajectories. The undersampling comes from the gap between adjacent interleaves (or adjacent turns for single shot acquisition).

The largest k-space radius free of undersampling artifacts, $k_0$, can be estimated from the Nyquist criterion, $2\pi k_0/N_{leaf}=1/FOV$, where $N_{leaf}$ is the number of interleaves. Slight undersampling artifacts may be tolerated, so the optimal k-space radius for constructing low resolution image for coil sensitivity estimation may be larger than $k_0=N_{leaf}/(2\pi FOV)$. For $N_{leaf}=24$, $k_0 \sim 4/FOV$.

The undersampling artifacts in spiral trajectories can be characterized through point spread function (PSF). The analytical expression for spiral PSF is too complicated to be instructive; instead we perform numerical simulation to investigate the relation between undersampling artifacts and the k-space size. For the identification of the optimal low resolution, SENSE images (I) are further characterized by image error defined as $$\varepsilon = \sum_{r \in ROI} ||I(r)| - I_0(r)|^2 \bigg/ \sum_{r \in ROI} I_0^2(r). \qquad [1]$$

Where $I_0$ is the fully-sampled image and the summation in Equation 1 is over a ROI determined by the outer bound of an object in the FOV. This global image error contains both error in coil sensitivity map due to lack of spatial detail and error due to undersampling artifacts; accordingly its minimization leads to an optimal selection for k-space radius in self-calibration.

Experiments were performed on both phantoms and human subjects on 1.5 Tesla whole body MRI scanner using uniform interleaved spiral sampling and 4-element coil arrays. The cardiac coil was used for the phantom and the torso coil for human subjects. Data collection parameters were 24 interleaves, 256×256 image size, and 12 cm FOV and 2872 pts/leaf for phantoms, 30 cm FOV and 1442 pts/leaf for human. Fully sampled k-space data sets were collected and 2× undersampled data, which are also the approximate k-space radius without aliasing artifacts, were derived from the full data sets by discarding the odd interleaves. The self-calibrated SENSE was performed using the 2× undersampled data. For comparison, the standard SENSE was performed using fully sampled data in the same k-space center. The criterion for the conjugate gradient iteration convergence 5 was set 0.0001 for both the self-calibrated SENSE and the standard SENSE.

Figure 11:
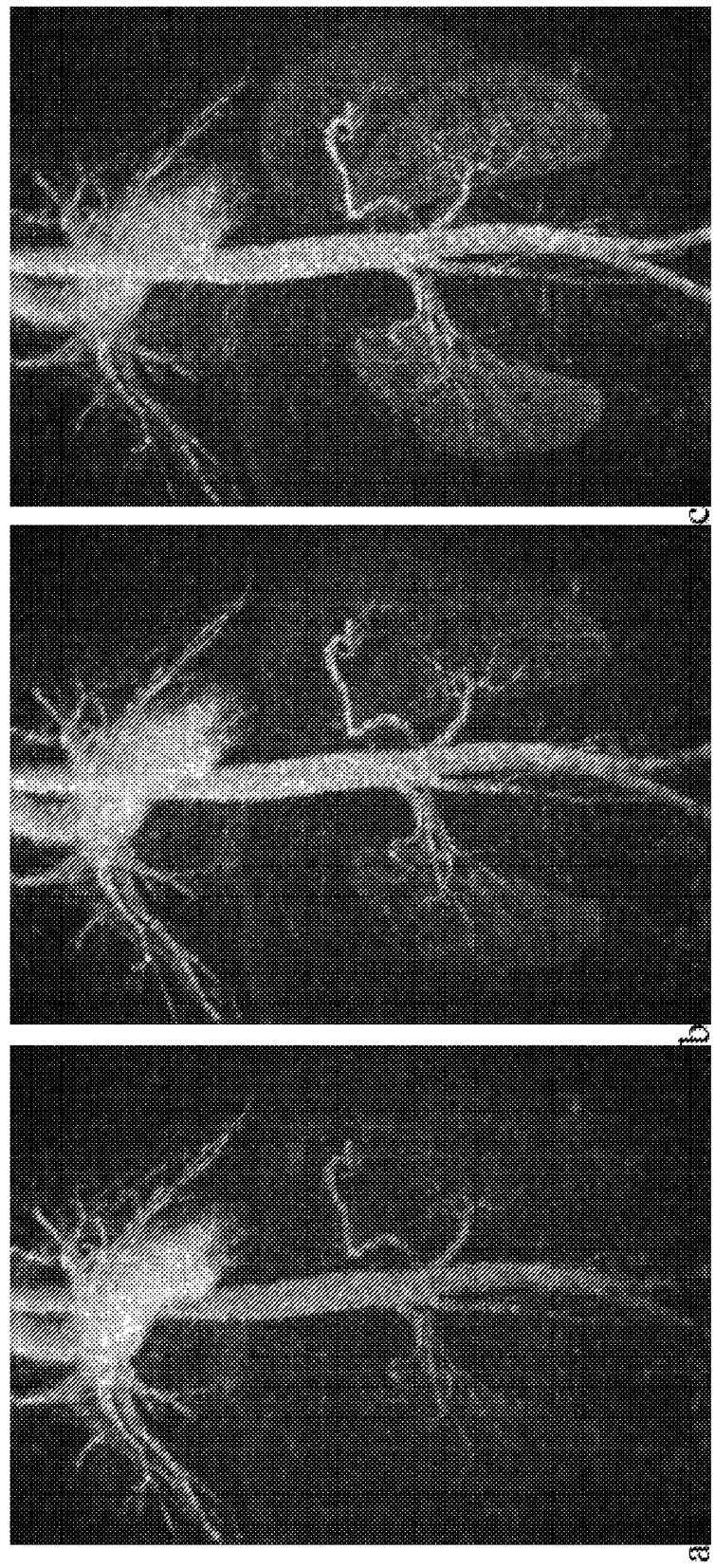
FIGS. 11A, 11B, and 11C display a time-resolved 3D MRA of the chest and abdomen acquired at 2 seconds per frame using a body coil and 5 cc Gd at 1 cc/second delineating the mesenteric arteries and associated organ enhancements.
Figure 17:
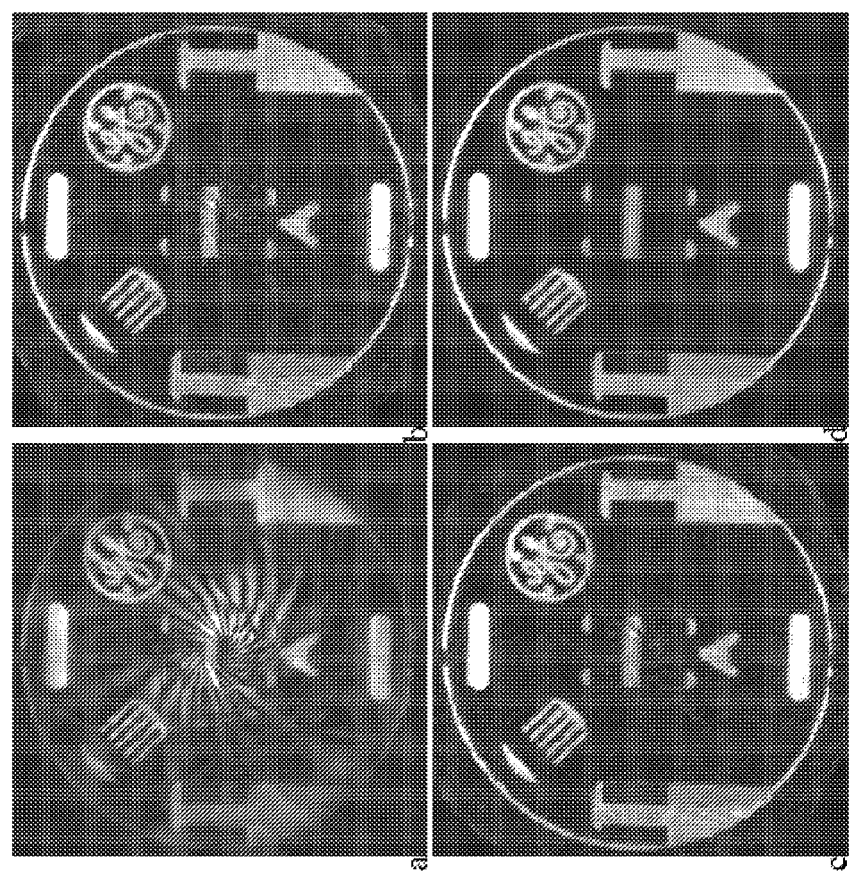
FIGS. 17A-D display phantom images (17A) sum of squares image obtained from the 2× undersampled data using the standard gridding algorithm; (17B) self-calibrated SENSE image (k-space radius=4/FOV, 12 iterations); (17C) corresponding standard SENSE image, (11 iterations), and (17D) sum-of-squares image obtained from the fully sampled k-space data using the standard gridding algorithm.

The PSFs for the 2× undersampled k-space at various k-space radii (2, 3, 4, 5, & 6/FOV) are illustrated in FIGS. 15A-E. The intensity of the undersampling streaking artifacts increased as the reconstruction k-space radius increased. The streaking artifacts were hardly visible at radii (2 & 3)/FOV but clearly appeared at radii (4, 5, & 6)/FOV, suggesting that 4/FOV might be approximately the threshold radius for tolerable undersampling artifacts for the spiral trajectory in FIG. 15F. That point was further confirmed in the image error analysis (FIG. 16), which demonstrated that the low resolution images at 4/FOV were similarly compared to the 2× undersampled (FIGS. 16A-D) and the fully sampled data (FIGS. 16E-H). For the phantom experiment, the self-calibrated SENSE generated images (FIG. 17B, 12 iterations) of quality similar to the standard SENSE (FIG. 17C, 11 iterations). Compared to the fully sampled image (FIG. 17D), the self-calibrated SENSE contained an image error of 6.3%, and the standard SENSE contained an image error of 5.6%. FIG. 17A displays a sum-of-squares image obtained from the 2× undersampled data using the standard gridding algorithm. The SNR of the self-calibrated SENSE image was 25.2; the SNR of the standard SENSE image was 25.5, and the SNR of the fully sampled image was 42.0. The SNR reductions for both SENSE images were 60% (corresponding average g-factor 1.18).

Figure 18:
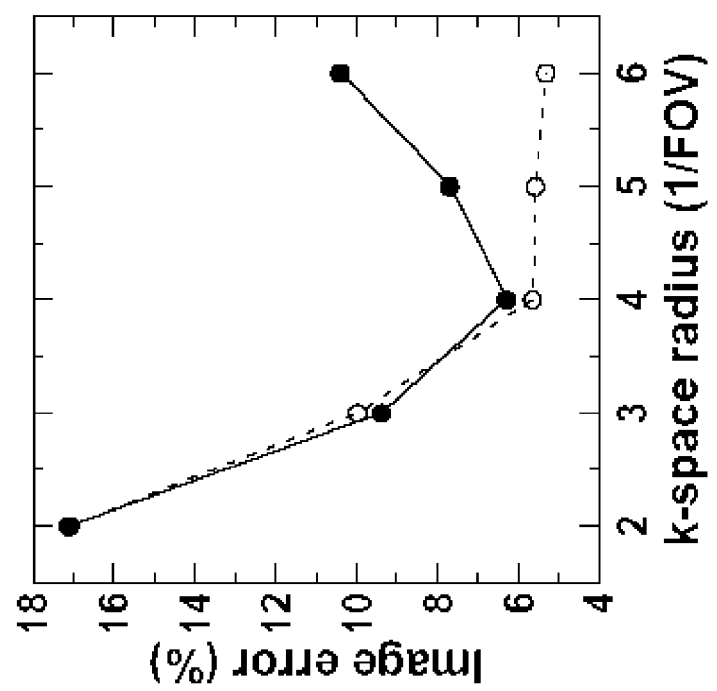
FIG. 18 shows image error vs. k-space size of the sensitivity map for both the self-calibrated SENSE (solid line) and the standard SENSE (dashed line) using the reconstructions of the sample images in FIG. 17.

The image error of the self-calibrated SENSE varied with the radius of the k-space center (FIG. 18, solid line). The image error decreased from 17.1% at radius 2/FOV to a minimum (6.3%) at radius 4/FOV, and then increased to 10.4% at radius 6/FOV. The V-shape of the solid line suggested two main sources were responsible for the self-calibrated SENSE image error: the spatial frequency cutoff of the coil sensitivities at small k-space radii and the undersampling artifacts at large radii. The image error of the standard SENSE (FIG. 18, dashed line) fell sharply from 17.1% at radius 2/FOV to 5.6% at radius 4/FOV and then decreased slightly to 5.5% at 6/FOV. This observation suggests that the effect of the spatial frequency cutoff on the image error was negligible at radii 4/FOV and beyond.

Figure 19:
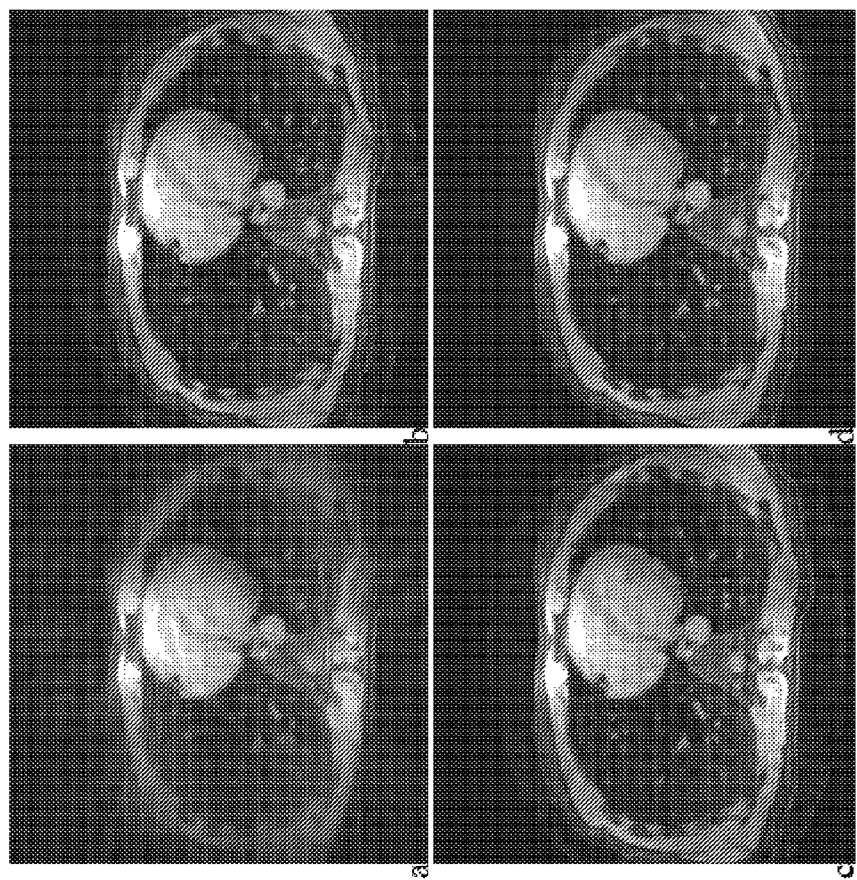
FIGS. 19A-D display (19A) sum-of-squares image of human heart obtained from the 2× undersampled data using the standard gridding algorithm; (19B) self-calibrated SENSE image (k-space radius=4/FOV, 6 iterations) of the human heart; (19C) corresponding standard SENSE image (6 iterations) of the human heart; and (19D) sum-of-squares image obtained from the fully sampled k-space data using gridding algorithm.

The self-calibrated spiral SENSE scheme of the present invention was then applied to human hearts (FIG. 19). FIG. 19A is a sum-of-squares image obtained from the 2× undersampled data using the standard gridding algorithm. FIG. 19B displays data from a self-calibrated SENSE image (K-space radius—4/FOV, six iterations. FIG. 19C displays the corresponding standard SENSE image (six iterations). FIG. 19D is a sum-of-squares image obtained from the fully sampled k-space data using the gridding algorithm. Both the self-calibrated SENSE and the prior art SENSE generated similar image quality (FIG. 19B vs. FIG. 19C) in the same number of iterations (n=6). Image errors were also computed for identifying the optimal k-space radius. The image error curve in FIG. 20 suggested the same 4/FOV radius for optimal self calibration with the 2× undersampled data. The error of the self-calibrated SENSE image was 0.9% at radius 4/FOV, the same as that of the prior art SENSE image. The SNR of the self-calibrated SENSE image was 37.3, very close to the SNR of the standard SENSE image (37.4). The SNR of the fully sampled image was 59.0. The SNR reductions for both SENSE were 63% (corresponding average g-factor=1.12).

Figure 20:
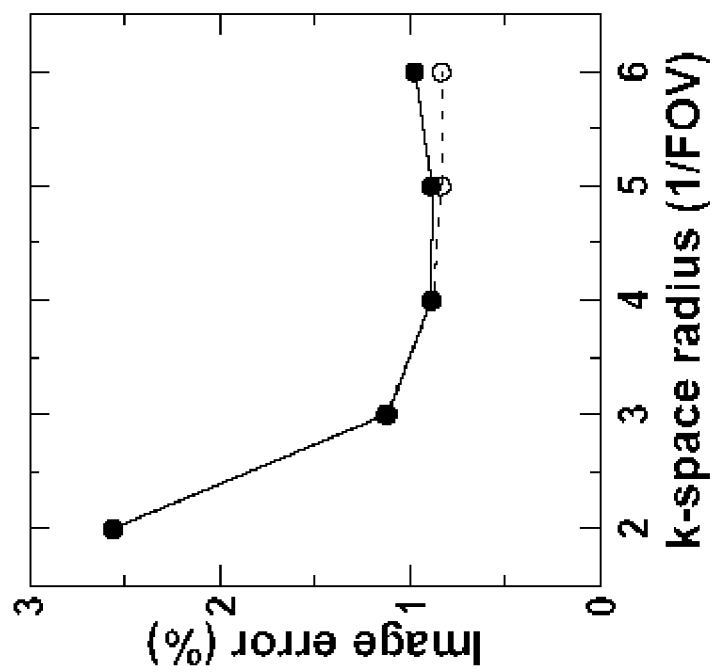
FIG. 20 displays image error vs. k-space size of the sensitivity map for both the self-calibrated SENSE (solid line) and the standard SENSE (dashed line) using the data in FIG. 19.

The minimal image error of the self calibrated SENSE is approximately the same as that of the standard SENSE (FIGS. 18 and 20, the actual minimum depending on the specific imaging situation). This result implies that the coil sensitivity spectrum has very small weighting beyond the spatial frequency radius 4/FOV (approximately the critical k-space radius, smaller than which there is no alias artifact). When the coil dimension diminishes, as in the case of an array with many coil elements, the coil sensitivity spectrum will spread over a large range of spatial frequencies. Consequently the image error in the self calibrated SENSE may become noticeably larger than that in the standard SENSE if the k-space radius is kept at 4/FOV. For such cases, a dense sampling trajectory with a correspondingly large k-space radius for optimal self calibration may be employed to achieve image quality comparable with the standard SENSE.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

We claim:

1. A method of acquiring magnetization prepared steady-state magnetic resonance imaging data from a tissue, comprising the steps of:
    defining a plane within k-space;
    dividing said plane within k-space into a plurality of pairs of radial wedges, wherein each pair of radial wedges has a common vertex at the center of k-space, further wherein each pair of radial wedges reside on opposite sides of the center of k-space, and further wherein said plurality of pairs of radial wedges represent all of said plane within k-space;
    collecting a series of images from said tissue by following a trajectory in k-space, wherein said trajectory comprises a first sequence of steps, wherein said first sequence comprises
        a first collection step across the width of the first of said first pair of radial wedges; and
        a second collection step along the border of said first of said first pair of radial wedges, wherein the second collection step is oriented towards the center of k-space;
    further wherein said first and second collection steps are repeated until said trajectory reaches the center of k-space,
    wherein said trajectory further comprises a second sequence of steps wherein said second sequence comprises
        a first collection step across the width of the second of said first pair of radial wedges; and
        a second collection step along the border of said second of said first pair of radial wedges, wherein the second collection step is oriented away from the center of k-space;
    further wherein said trajectory comprises a third sequence of steps wherein said third sequence comprises
        a third collection step across the width of said second of said first pair of radial wedges and further across the first of a second pair of radial wedges, wherein said second pair of radial wedges is adjacent to said first pair of radial wedges; and
        a fourth collection step along the border of said second of said first pair of radial wedges or along the border of said first of said second pair of radial wedges, wherein the second collection step is oriented away from the center of k-space.

2. The method of claim 1, wherein the trajectory traverses the center of k-space at a background nulling point.

3. A method of acquiring magnetization prepared steady-state magnetic resonance imaging data from a tissue, comprising the steps of:
    (a) for each of a plurality of segments into which k-space has been segmented:
        (1) enhancing contrast in the tissue; and
        (2) acquiring image data from the tissue using a segmented steady state free precession sequence along a trajectory comprising points in k-space, wherein:
            the points of the trajectory are:
                confined to the segment of k-space or to the segment of k-space and an adjacent segment of k-space; and
                include points in k-space center and k-space periphery;
            image data is acquired at all points in the trajectory before any image data is acquired along another trajectory; and
            points nearest the k-space center are acquired at a time corresponding to a maximal contrast enhancement; and
    (b) compiling the acquired image data into a magnetic resonance image;
    wherein acquisition of a first segment commences at a point intermediate between k-space center and an extreme of k-space periphery, and wherein the point intermediate between k-space center and the extreme of k-space periphery is selected such that the trajectory traverses the k-space center at a time corresponding to a background nulling point.

4. The method of claim 3, wherein adjacent points in a trajectory are collected at adjacent points in time.

5. The method of claim 3, wherein acquisition from a first segment is followed immediately by acquisition from a second segment diametrically opposed to the first segment across the k-space center.

6. The method of claim 5, wherein acquisition of the first segment proceeds toward the k-space center, and acquisition of the second segment proceeds away from k-space center.

7. The method of claim 6, wherein the first segment's trajectory is radially symmetrical to at least a portion of the second segment's trajectory.

8. The method of claim 3, wherein a trajectory comprises a series of segments that alternate between (a) radial orientation toward or away from k-space center and (b) oblique to radial orientation.

9. The method of claim 8, wherein the (b) segments span points in adjacent segments of k-space.

10. The method of claim 3, wherein for each segment, step (a)(1) comprises applying one or more preparatory radio-frequency pulses to create a steady-state.

11. The method of claim 10, wherein the one or more preparatory radio-frequency pulses include at least one inversion pulse nullifying signal from background tissue.

12. The method of claim 10, further comprising applying a fat saturation pulse during the steady state, after the one or more preparatory radio-frequency pulses and before image data acquisition.

13. The method of claim 12, further comprising applying a navigator pulse during the steady state, after the one or more preparatory radio-frequency pulses and before image data acquisition.

14. The method of claim 10, further comprising applying at least one radio-frequency pulse having a flip angle equal to half of that of the pulses applied to create the steady-state.

15. The method of claim 10, further comprising applying radio-frequency pulses temporally separated by repetition time and having flip angles sequentially increasing to that of the pulses applied to create the steady-state.

16. The method of claim 3, further comprising applying a navigator pulse before image data acquisition, acquiring therefrom a signal indicative of motion of the tissue, and suppressing motion artifacts in the image data thereby.

17. The method of claim 16, wherein suppressing comprises gating image data acquisition based on the motion signal to minimize residual motion artifacts.

18. The method of claim 17, wherein suppressing further comprises compensating for three-dimension motion using affine motion correction.

19. The method of claim 16, wherein trajectory point order is determined in part based on the motion signal.

20. The method of claim 3, wherein the tissue comprises a heart and image data acquisition is triggered by an electrocardiogram signal so that image acquisition is cardiac phase-resolved imaging.

21. The method of claim 3, wherein a plurality of coils is used for image data acquisition, data acquisition is accelerated using undersampling, and image data is reconstructed using a SENSE algorithm.

22. The method of claim 3, wherein the image data is acquired and compiled using a sliding window algorithm.

* * * * *